United States Patent [19]

Gagné et al.

[11] Patent Number: 5,539,048

[45] Date of Patent: Jul. 23, 1996

[54] MACROMONOMERS HAVING REACTIVE SIDE GROUPS

[75] Inventors: Robert R. Gagné, Pasadena; Matthew L. Marrocco, III, Santa Ana; Mark S. Trimmer, Pasadena; Neil H. Hendricks, Brea, all of Calif.

[73] Assignee: Maxdem Incorporated, San Dimas, Calif.

[21] Appl. No.: 458,501

[22] Filed: Jun. 2, 1995

Related U.S. Application Data

[62] Division of Ser. No. 746,883, Aug. 19, 1991.

[51] Int. Cl.⁶ .................................................. C08G 6/00
[52] U.S. Cl. ........................... 525/50; 525/55; 525/390; 525/416; 525/417; 525/418; 525/419; 525/452; 525/509; 525/523; 525/540
[58] Field of Search ........................... 525/50, 390, 416, 525/417, 523, 540, 418, 419, 452, 509

[56] References Cited

U.S. PATENT DOCUMENTS

| | | | |
|---|---|---|---|
| 2,301,206 | 11/1942 | France et al. | 585/427 |
| 2,809,210 | 10/1957 | Short et al. | 585/427 |
| 3,728,409 | 4/1973 | Selwitz | 585/427 |
| 3,748,350 | 7/1973 | Josephson et al. | 585/427 |
| 3,756,982 | 9/1973 | Vladimirovich et al. | 585/427 |
| 3,792,099 | 7/1974 | Wang et al. | 529/396 |
| 3,998,864 | 12/1976 | Trevillyan | 260/439 |
| 4,000,187 | 12/1976 | Stille | 528/125 |
| 4,008,266 | 2/1977 | Intille | 585/427 |
| 4,174,447 | 11/1979 | Fields | 585/427 |
| 4,720,576 | 1/1988 | Wada et al. | 585/427 |
| 4,885,423 | 12/1989 | Rule | 585/427 |
| 4,911,801 | 3/1990 | Pons | 528/397 |
| 5,102,971 | 4/1992 | Himmler et al. | 528/167 |
| 5,169,929 | 12/1992 | Tour et al. | 528/397 |
| 5,227,457 | 7/1993 | Marrocco, III et al. | 528/183 |

FOREIGN PATENT DOCUMENTS

| | | |
|---|---|---|
| 1129418 | 8/1982 | Canada . |
| 0130056 | 1/1985 | European Pat. Off. . |
| 3821567 | 12/1989 | Germany . |
| 1259030 | 10/1989 | Japan . |
| 2113023 | 4/1990 | Japan . |
| 0596569 | 3/1978 | U.S.S.R. . |
| 928576 | 6/1963 | United Kingdom . |
| 9005754 | 5/1990 | WIPO . |
| 9102764 | 3/1991 | WIPO . |

OTHER PUBLICATIONS

Rehahn et al., "Soluble Poly(para–phenylene)s. 1. Extension of the Yamamoto Synthesis to Dibromobenzenes Substituted with Flexible Side Chains," *Polymer* (Jun. 1989), pp. 1054–1059.
Mezhikovskii et al, Chem. Abs., 78:98152j, 1973.
English–language version of 78:98152j, Mezhikovskii et al, "Thermal and Thermo–Oxidative Degradation of Polysulphophenylenequinonones," *Vysokomol. soyed.*, A14: No. 11, 2397–2404, Nov. 1972.
Trevillyan, Chem. Abs., 86:139404d, 1977.
Liogon'kii et al, Chem. Abs, 96:7293p, 1982.
Matnishyan et al., "The Effect of Various Factors on the Synthesis of Polyarylenequinones," *Vysokomol. soyed.*, A13: No. 5, 1009–1017, May 1971.
Wallow et al, Chem. Abs., 115:280696z, 1991.
Wallow et al, Chem. Abs., 115:136902w, 1991.
Wallow et al, "Aqueous Synthesis of Soluble Rigid–Chain Polymers, An Ionic Poly(p–phenylene) Analog," *Polymer Preprints, American Chemical Society*, vol. 32, No. 3, Pub. Date Aug. 12, 1991.
Kallitsis et al, "Synthesis of Some Di–substituted Poly(p–terphenylenes)," *Synthetic Metals*, 44 (1991) 247–257.
Kallitsis et al, Chem. Abs., 116:21589c, 1992.

*Primary Examiner*—Jeffrey Mullis
*Attorney, Agent, or Firm*—Christie, Parker & Hale

[57] ABSTRACT

Rigid-rod macromonomers, and methods for preparing such macromonomers, having a polyaromatic backbone, solubilizing side groups, and reactive side groups are provided. The macromonomers are chemically incorporated into polymer systems to provide stronger, stiffened polymers.

21 Claims, 2 Drawing Sheets

MACROMONOMERS HAVING REACTIVE SIDE GROUPS

CROSS-REFERENCE TO RELATED APPLICATION

This is a division of application Ser. No. 07/746,883 filed Aug. 19, 1991.

FIELD OF THE INVENTION

This invention relates to soluble macromonomers having rigid-rod backbones, pendant, flexible, solubilizing organic groups attached to the backbone, and pendant reactive groups attached to the backbone of the macromonomer chains. They can be chemically incorporated into other polymer and monomer systems to yield strengthened, stiffened polymer compositions.

BACKGROUND OF THE INVENTION

It is well known that the stiffness and strength of a polymer are related to the flexibility of the polymer chain on the molecular level. Thus, if the chemical structure of the main chain restricts chain coiling and flexing, the resulting polymer will be stiff and strong. An example of a stiff polymer is poly-1,4-phenylene-1,4-terephthalamide (PPTA). While PPTA can coil in solution, the amide linkages and para-phenylene groups favor an extended chain conformation. Fibers can be prepared in which the chains are essentially all extended into rod-like conformations, and these fibers are extraordinarily strong and stiff. Unfortunately, PPTA is difficult to process (except for fiber spinning) and cannot be molded or extruded. In general, the more rigid the polymer main chain the more difficult it is to prepare and process.

Some applications require strong, stiff materials that can be easily processed by molding or extrusion. A widely used approach to obtain such stiff materials is to add fillers such as carbon or silica, or to incorporate fibers, such as glass and carbon fibers, into a relatively flexible polymer, thereby forming a stiff, strong composite material. The most widely utilized, high-performance fiber-polymer composites are composed of oriented carbon (graphite) fibers embedded in a suitable polymer matrix.

The improvements in strength and stiffness of composites are related to the aspect ratio of the filler or fiber, i.e., the length to diameter ratio of the smallest diameter cylinder that will enclose the filler or fiber. To contribute reasonable strength and stiffness to the composite, the fibers must have an aspect ratio of at least about 25, and preferably at least 100. Continuous fibers have the highest aspect ratio and yield the best mechanical properties but are costly to process. Low aspect ratio materials, such as chopped fibers and fillers, give limited improvement in mechanical properties, but are easy and inexpensive to process. The success of composites is demonstrated by their wide use as structural materials.

There are several drawbacks associated with composite materials. Composites are often more costly than the unreinforced polymer. This is because of the expense of the fiber component and the additional labor needed to prepare the composite. Composites are difficult or impossible to repair and in general cannot be recycled. Many composites also have undesirable failure characteristics, failing unpredictably and catastrophically.

Molecular composites (composed of polymeric materials only) offer the prospect of high performance, lower cost and easier processability than conventional fiber-polymer composites. In addition, molecular composites generally can be recycled and repaired. Because molecular composites contain no fibers, they can be fabricated much more easily than fiber-polymer compositions, which contain macroscopic fibers.

Molecular composites are materials composed of a rigid-rod polymer embedded in a flexible polymer matrix. The rigid-rod polymer in a molecular composite can be thought of as the microscopic equivalent of the fiber in a fiber-polymer composite. The flexible polymer component of a molecular composite serves to disperse the rigid-rod polymer, preventing bundling of the rigid-rod molecules. As in conventional fiber/resin composites, the flexible polymer in a molecular composite helps to distribute stress along the rigid-rod molecules via elastic deformation of the flexible polymer. Thus, the second, or matrix-resin polymer must be sufficiently flexible to effectively surround the rigid-rod molecules while still being able to stretch upon stress. The flexible and rigid-rod polymers can also interact strongly via Van der Waals, hydrogen bonding, or ionic interactions. The advantages of molecular composites over fiber-based composites are realized by incorporating rigid-rod segments into polymer systems. The advantages of molecular composites have been demonstrated by, e.g., W. F. Hwang, D. R. Wiff, C. L. Benner and T. E. Helminiak, *Journal of Macromolecular Science.—Phys.*, B22, 231–257 (1983).

Molecular composites are simple mixtures or blends of a rigid-rod polymer with a flexible polymer. As is known in the art, most polymers do not mix with other polymers, and attempts at blends lead to macroscopic phase separation. This is also true of rigid-rod polymer/flexible polymer blends. Metastable blends may be prepared by rapid coagulation from solution. However, metastable blends will phase separate on heating, ruling out further thermal processing, such as molding or melt spinning and use at high temperatures. The problem of macroscopic phase separation is reported in H. H. Chuah, T. Kyu, and T. E. Helminiak, *Polymer*, 28, 2130–2133 (1987). Macroscopic phase separation is a major limitation of molecular composites.

Rigid-rod polymers produced in the past are, in general, highly insoluble (except in the special case of polymers with basic groups, which may be dissolved in strong acids or in organic solvents with the aid of Lewis acids) and infusible. Preparation and processing of such polymers is, accordingly, difficult. A notable exception is found in U.S. patent application Ser. No. 07/397,732, filed Aug. 23, 1989 (assigned to the assignee of the present invention), which is incorporated herein by this reference. The rigid-rod polymers described in the above-referenced application have a rigid-rod backbone comprising a chain length of at least 25 organic monomer units joined together by covalent bonds wherein at least about 95% of the bonds are substantially parallel; and solubilizing organic groups attached to at least 1% of the monomer units. The polymers are prepared in a solvent system that is a solvent for both the monomer starting materials and the rigid-rod polymer product. The preferred monomer units include: paraphenyl, parabiphenyl, paraterphenyl, 2,6-quinoline, 2,6-quinazoline, paraphenylene-2-benzobisthiazole, paraphenylene-2-benzobisoxazole, paraphenylene-2-benzobisimidazole, paraphenylene-1-pyromellitimide, 2,6-naphthylene, 1,4-naphthylene, 1,5-naphthylene, 1,4-anthracenyl, 1,10-anthracenyl, 1,5-anthracenyl, 2,6-anthracenyl, 9,10-anthracenyl, and 2,5-pyridinyl.

The rigid-rod polymers described above can be used as self-reinforced engineering plastics and exhibit physical properties and cost-effectiveness superior to that exhibited by many conventional fiber-containing composites. It would be quite useful if rigid-rod polymers could be incorporated into conventional flexible polymers, especially large volume commodity polymers. The value of a flexible polymer would be increased significantly if its mechanical properties could be enhanced by addition of rigid-rod polymers. Such molecular composites could displace more expensive engineering resins and specialty polymers and conventional composites as well. To date, practical molecular composites have not been demonstrated. This is chiefly due to deficiencies in currently available rigid-rod polymers, namely, limited solubility and fusibility and unfavorable chemical and physical interactions between the rigid-rod and the flexible polymer component.

There is a need in the art for a rigid-rod polymer that can be chemically incorporated into flexible polymers and polymer systems, during or subsequent to polymerization, to thereby add strength and/or stiffness to the resulting polymers. Chemical rather than physical incorporation is desirable to inhibit phase separation during the processing and use of the polymer and to increase the resulting polymer's solvent resistance. The mechanical behavior of polymer systems which contain chemically incorporated rigid-rod moieties can be different and superior to physical blends of, for example, rigid-rod polymers with flexible polymers.

SUMMARY OF THE INVENTION

It has now been found that, for any given polymer, improvements in stiffness and strength can be obtained by preparing a copolymer, thermoset resin, or the like, which incorporates rigid segments and the more flexible segments of the original polymer. These rigid segments act in a manner conceptually similar to the way stiff fibers act to reinforce composites; however, in the present invention no macroscopic fibers are present.

In the present invention, the problem of macroscopic phase separation, found in molecular composites, is avoided by the use of rigid-rod macromonomers having reactive side groups. In one embodiment of the present invention, the rigid-rod macromonomers are made to react with flexible polymers, via reactive side groups, to form covalent bonds between the rigid-rod macromonomer and the flexible polymer, thereby preventing macroscopic phase separation.

In a second embodiment, macroscopic phase separation is prevented by forming the flexible polymer in the presence of the macromonomer. The reactive side groups of the macromonomer react with monomers during polymerization of the flexible polymer, forming covalent bonds between the macromonomer and flexible polymer.

In a third embodiment, the rigid-rod macromonomer is modified, by way of chemical transformation of its reactive side groups, such that the side groups are made compatible with the flexible polymers. Compatibilizers include groups which will interact with the flexible polymer ionically, by hydrogen bonding, or by van der Waals interactions. Compatibilizers may be polymeric or oligomeric. For example, a rigid-rod macromonomer may be made to react, via its reactive side groups, with caprolactam to form short polycaprolactam chains at various locations along the macromonomer chain, the resulting polycaprolactam-modified macromonomer being compatible with polycaprolactam.

It should be understood that while macroscopic phase separation is prevented, there may be varying degrees of microscopic phase separation. Microscopic phase separation results in the formation of phases that have sizes on the order of the dimensions of the polymer chain. Microphase separation may be conducive to significant improvements in mechanical or other properties desired from incorporation of rigid-rod macromonomers.

In a fourth embodiment, the rigid-rod macromonomers are used alone as thermosetting resins. In this case, the side groups provide some degree of processability and will react under the appropriate conditions (e.g. heat, irradiation, exposure to air, etc.) to form crosslinks and effect curing.

In a fifth embodiment, the rigid-rod macromonomers are used to modify ceramics and inorganic glasses, using sol-gel or other methods known in the art. Here, the reactive side groups undergo special interactions with the inorganic matrix, either polar, ionic or covalent.

Other methods of incorporating the rigid-rod macromonomers of the present invention into materials are contemplated and depend on the chemistry and properties of the material to be modified.

In one embodiment of the invention, the macromonomers have the structure (1):

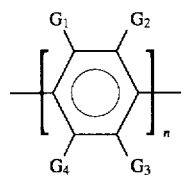

(1)

where each $G_1$, $G_2$, $G_3$, and $G_4$, on each monomer unit, independently, is either hydrogen, a solubilizing side group, or a functional ("reactive") side group, and the number average degree of polymerization, $DP_n$, is greater than about 6. If $DP_n$ is less than about 7 or 8, the rigidity and stiffness of polymers incorporating such macromonomers are only slightly increased. Preferably, $DP_n$ is between 10 and 500. In some applications, however, macromonomers prepared in accordance with the present invention having a $DP_n$ as low as 4 may be useful, for example, as a means of decreasing the thermal expansion coefficient of a flexible polymer, such as a polyimide or a polyamide.

At least one monomer unit in the macromonomer has at least one reactive side group or reactive solubilizing side group. A description of such groups is provided below.

The structures presented here show only a single monomer unit and do not imply regular head-to-tail arrangement of monomer Units along the chain. Monomer units may have random orientation or may be alternating head-to-head, tail-to-tail, or regular head-to-tail, or have other arrangements, depending on the conditions of the polymerization and reactivity of monomers.

The macromonomers of the present invention may also contain heteroatoms in the main chain. Heteroaromatic rigid-rod macromonomers have structure (2), where $A_1$, $A_2$, $A_3$, and $A_4$ on each monomer unit, independently, may be carbon or nitrogen, and each G is as defined above, except that where an A is nitrogen, the corresponding G is nil.

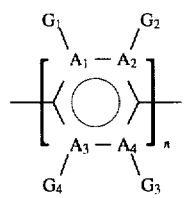

(2)

As with structure (1), the macromonomers of structure (2) have at least one monomer unit that has at least one reactive side group or reactive solubilizing side group.

Other rigid-rod monomer units can also be incorporated into the macromonomers prepared in accordance with the present invention. Thus a rigid-rod macromonomer having monomer units of the type shown in structures (1) and/or (2) and benzobisthiazole monomer units

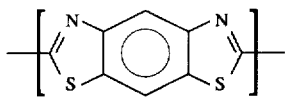

can be used in the same way as (1) and (2). Likewise, rigid-rod pyromellitimide, benzobisoxazole, benzobisimidazole and other rigid-rod monomer units may be substituted for some of the phenylene units without loss of function. The benzobisimidazole, thiazole and oxazole units may have either a cis or trans configuration.

The rigid-rod macromonomers of the present invention may be further polymerized or cured by virtue of their reactive side groups. Depending on the nature of the side groups and cure conditions, branched, network, or other structures result.

The macromonomers of the present invention may be used to form thermosets, either alone or in combination with other thermosetting polymers. The macromonomers may also be used with thermoplastics, e.g., by forming a copolymer.

DETAILED DESCRIPTION OF THE INVENTION

Figure 1:
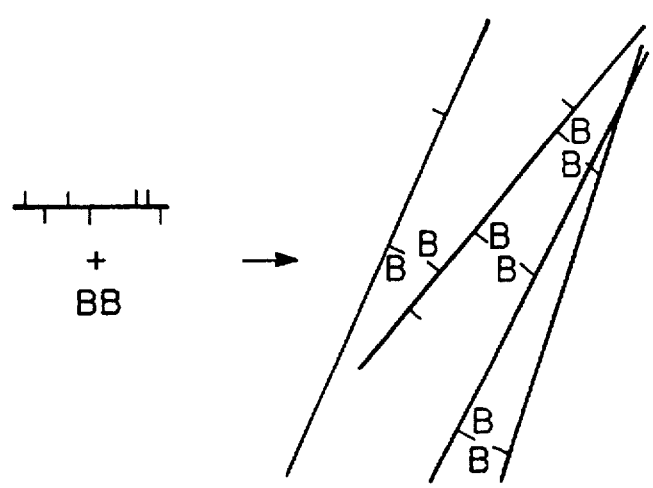
FIG. 1 is a schematic illustration of the formation of a crosslinked polymer prepared by reacting macromonomers of the present invention with one species of complementary monomers.

As discussed above, the strength and stiffness of a polymer are related to the flexibility of the polymer chain on a molecular level. It has now been found that for any given polymer, improvements in stiffness and strength can be obtained by preparing a copolymer having rigid segments as well as the more flexible segments of the original polymer. These rigid segments act in a manner conceptually similar to the way stiff fibers act to reinforce composites, however, in the present invention no macroscopic fibers are present. The rigid segments are provided by incorporating rigid-rod macromonomers having structures (1) and/or (2) during or subsequent to polymerization of the flexible polymer. Several approaches are provided by the present invention.

Macromonomers having structure (1) are solubilized polyparaphenylenes having reactive functional side groups. Macromonomers having structure (2) are aza derivatives of polyparaphenylenes having reactive side groups. In each case, $G_1$ through $G_4$ are solubilizing side groups, functional side groups, or hydrogen, and the number average degree of polymerization, $DP_n$, is greater than about 6, preferably between 10 and 500.

The terms "reactive side group," "functional side group," and the like are defined to mean any chemical moiety attached to the backbone of a rigid-rod macromonomer molecule, which chemical moiety can be used in a subsequent reaction to effect one or more of the following reactions:

a) Reaction with a flexible polymer resulting in formation of one or more covalent bonds between the macromonomer and the flexible polymer;

b) Reaction with monomers, either before or during a reaction in which such monomers are polymerized to give a flexible polymer, resulting in formation of one or more covalent bonds between the macromonomer and the resulting flexible polymer;

c) Reaction with an oligomer or other small molecular species, resulting in increased compatibility of the rigid-rod macromonomer with flexible polymers in blends, mixtures, composites, copolymers, composites, alloys and the like; and d) Polar, ionic, or covalent interaction with an inorganic matrix, resulting in a modified ceramic or an inorganic glass or glass-like material.

Reactive groups may be transformed by further chemical reaction, including without limitation, oxidation, reduction, deprotonation, halogenation, Schiff base formation, hydrolysis, electrophilic or nucleophilic substitution, and the like, to yield new reactive groups.

One skilled in the art will recognize that it sometimes will be desirable to incorporate such reactive side groups in a protected form in order to ensure that the reactive group does not poison or otherwise participate in or interfere with the macromonomer-forming reaction, e.g., an amine can be incorporated as an amide, a carboxylic acid can be incorporated as an ester, and an alcohol can be incorporated as an ester or as an ether. Once formation of the macromonomer has been completed the protected reactive side group can then be deprotected, e.g., an amide or an ester can be hydrolyzed to produce an amine and an alcohol, respectively.

Non-limiting examples of reactive side groups include acetals, acetals from ethylvinylether, acetylenes, acetyls, acid anhydrides, acids, acrylamides, acrylates, alcohols, aldehydes, alkanols, alkyl aldehydes, alkyl ketones, amides, amines, alkyl halides, anilines, aryl aldehydes, aryl ketones, azides, benzocyclobutenes, biphenylenes, carbonates, carboxylates, carboxylic acids and their salts, carboxylic acid halides, carboxylic anhydrides, cyanates, cyanides, epoxides, esters, ethers, formyls, fulvenes, halides, heteroaryls, hydrazines, hydroxylamines, imides, imines, isocyanates, ketals, ketoalkyls, ketoaryls, ketones, maleimides, nadimides, nitriles, olefins, phenols, phosphates, phosphonates, quaternary amines, silanes, silicates, silicones, silyl ethers, styrenes, sulfonamides, sulfones, sulfonic acids and their salts, sulfonyl halides, sulfoxides, tetrahydropyranyl ethers, thioethers, urethanes, vinyl ethers, vinyls and the like. In some cases, the functional side groups are capable of reacting with each other. Reactive side groups may be oligomeric or polymeric. Reactive side groups may also be bridging groups, such as —$CH_2CH=CHCH_2$—.

One skilled in the art will recognize that reactive groups can be prepared from "non-reactive" groups and "less reactive" groups. For example, some applications make it desirable to incorporate a rigid-rod polymer having tolyl end groups into a flexible polyester. The tolyl group is unreactive toward polyesters or polyester monomers, however, the tolyl group can be oxidized to a reactive carboxyphenyl group which then can react with polyesters by trans-esterification or with polyester monomers to form polyesters containing the rigid-rod macromonomer. Similarly, a relatively non-reactive acetyl group can be modified by formation of a Schiff's base with 4-aminophenol, to give a macromonomer having phenolic end groups, useful for reinforcing thermoset resins such as epoxies and phenolics. Other examples will be apparent to those skilled in the art.

The term "solubilizing side group" as used herein means a chemical moiety which, when attached to the backbone of the macromonomer, improves the solubility of the macromonomer in an appropriate solvent system. For the purposes of the present invention, the term "soluble" will mean that a solution can be prepared containing greater than 0.5% by weight of the macromonomer or greater than about 0.5% of the monomer(s) being used to form the macromonomer.

One skilled in the art will appreciate that various factors must be considered in choosing a solubilizing group for a particular polymer and solvent, and that, all else being the same, a larger or higher molecular weight solubilizing group will induce a higher degree of solubility. Conversely, for smaller solubilizing groups, matching the properties of the solvent and solubilizing groups is more critical, and it may be necessary to have, in addition, other favorable interactions inherent in the structure of the polymer to aid in solubilization.

For the macromonomers of the present invention any given non-hydrogen side group G can act as a solubilizing group, a reactive group, or both a solubilizing and reactive group; the latter being referred to as a reactive solubilizing group.

The number average degree of polymerization, $DP_n$, is defined by:

$DP_n$=(number of monomer molecules present initially)/(number of polymer or oligomer chains in the system).

The number average molecular weight, $M_n$ is defined by:

$M_n = M_o \times DP_n$ where $M_o$ is the weight of one monomer unit in the chain.

The number average degree of polymerization $DP_n$ is indicated in structural formulae, as in structure (1), by "n".

Compounds having structure (1) or (2) are solubilized rigid-rod macromonomers having reactive side groups. Such macromonomers are rigid or stiff on both the microscopic and macroscopic level. These macromonomers can be incorporated into other polymers via the side groups G which are reactive side groups and will impart stiffness and strength to the resultant polymers. The distinction between oligomers and polymers is that the properties of an oligomer change measurably on changing the degree of polymerization by one, while for a polymer adding an additional monomer unit has little effect on properties. Since the range of $DP_n$ (>6) considered here covers both oligomers and polymers, and since this technical distinction is not of great importance to the applications of these compounds, we will use the term macromonomer to imply the entire range from oligomers to polymers.

In macromonomers having structure (2), if only one of the A's is nitrogen, for example if $A_4$ is N, substituted polypyridines of structure (3) result:

(3)

If only $A_1$ and $A_2$ are N, the monomer unit is a pyridazine; if only $A_1$ and $A_3$ are N, the monomer unit is a pyrazine, if only $A_1$ and $A_4$ are N, the monomer unit is a pyrimidine. If three A's are N, the monomer unit is a triazine. Other heterocyclic monomer units are included if some of the G's are bridging, for example, if $G_1$ and $G_2$ are —CHCH-CHCH—, and $A_3$ is N, the monomer unit is an isoquinoline.

Macromonomers having the structure (2) include compounds of the structure (1) as a subset.

It is possible to have rigid-rod macromonomers in accordance with the present invention comprising several types of monomer units, each with a different set of A's and G's, i.e., each $A_1$, $A_2$, $A_3$ and $A_4$ on each monomer unit, independently is C or N, and each $G_1$, $G_2$, $G_3$, and $G_4$ on each monomer unit, independently is H, a solubilizing side group, or a reactive side group. In other words, adjacent monomer units need not be identical. Macromonomers comprised of different monomers are copolymer-type macromonomers.

As stated above, the number and type of side groups necessary to impart solubility will depend on n and the nature and number of reactive side groups. If n is small, only a few side chains will be needed for solubility. That is, only some of the monomer units in each chain may be substituted; the rest are either unsubstituted, i.e., the G's are all H, or are non-solubilizing reactive side groups. Where n is very small and the reactive side groups aid solubility, few "solubilizing" side groups are required. Where n is large, solubility may be maintained by using more non-H G's per chain or by using G's with higher molecular weight. In many cases, the macromonomer will have exactly one non-hydrogen G per monomer unit, i.e. $G_1$=solubilizing and/or reactive side group, and $G_2=G_3=G_4$=H. Structures (1) and (2) are meant to imply both homopolymers and copolymers where not all monomer units have the same set of G's.

Depending on relative reactivity of the reactive side groups, the number of reactive side groups, the concentrations of flexible polymer or monomer and macromonomer, and the like, various structures of rigid-rod reinforced polymeric composition will be obtained. At one extreme, the rigid rod macromonomer will form one or more bonds at each monomer unit, so that many reactive groups per rigid rod chain are used, and many crosslinks are made between the rigid rod macromonomer and flexible polymer. Such highly crosslinked structures will be most useful as thermosets and should be processed accordingly (the majority of the crosslinks should be made after the material has been shaped or formed; i.e., macromonomers and flexible monomers are reacted in a mold or applied as a coating and then cured; macromonomers, flexible polymers and a catalyst are mixed, shaped and cured; etc.)

At the other extreme, only a few reactive side groups per macromonomer chain are available to form crosslinks, and a thermoplastic structure resembling a graft copolymer results. In one embodiment, each rigid-rod chain has many reactive side groups, but their reactivity is low under a predetermined set of conditions, and only some of the reactive groups participate in crosslinking, the rest remain unreacted. In another embodiment, in addition to macromonomers and a flexible polymer, a third component is added, which third component will cap some of the reactive groups, rendering them inert. This approach is useful for tailoring one type of macromonomer for different applications requiring different degrees of crosslinking. In another embodiment, each macromonomer chain has only a few reactive side groups, the rest being inert under processing conditions.

It will be recognized by one skilled in the art that a particular side group may be inert in one circumstance and reactive in another. For example, an amide side group may be reactive under conditions of transamidation, and able to form covalent bonds with flexible polyamides, but inert toward non-amide polymers such as polystyrene or polyvinylchloride.

The macromonomers of the present invention may interact differently with different classes of flexible polymers, for example, addition polymers and condensation polymers. A non-limiting list of flexible polymers that can incorporate the macromonomers of the present invention includes polyacetals, polyamides, polyimides, polyesters, polycarbonates, polyamide-imides, polyamide-esters, polyamide ethers, polycarbonate-esters, polyamide-ethers, polyacrylates; elastomers such as polybutadiene, copolymers of butadiene with one or more other monomers, butadiene-acrylonitrile rubber, styrene-butadiene rubber, polyisoprene, copolymers of isoprene with one or more other monomers, polyphosphazenes, natural rubber, blends of natural and synthetic rubber, polydimethylsiloxane, copolymers containing the dimethylsiloxane unit, polydiphenylsiloxane, copolymers containing the diphenylsiloxane unit; polyalkylmethacrylates, polyethylene, polypropylene, polyphenylene oxide, polyphenylene sulfide, polystyrene, polyvinylacetate, polyvinylalcohol, and polyvinylchloride.

Reinforcing Condensation Polymers

Rigid segments may be introduced into a wide variety of condensation polymers through the use of the rigid-rod macromonomers of the present invention. In one embodiment, the macromonomer is added during the polymer-forming reaction (polymerization) of the polymer to be stiffened. The polymer to be stiffened and/or strengthened will be referred to as the flexible polymer, regardless of its absolute stiffness. In one embodiment, in addition to being rigid, the macromonomer will dissolve in the flexible polymer polymerization dope and have functionality enabling it to take part in the polymerization reaction. In another embodiment, the initially formed flexible condensation polymer is isolated, and a solvent is selected for both the macromonomer and the flexible polymer. The flexible polymer and macromonomer are redissolved, and the macromonomer reacts with the originally formed flexible polymer. Macromonomers may also be dissolved in the melt of the flexible polymer, where reaction of the side groups may then occur.

Several types of condensation polymers may be distinguished. Condensation polymers may include a single monomer, usually referred to as an A-B monomer:

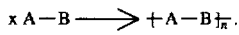

Alternatively, two complementary difunctional monomers, usually referred to as A-A and B-B may be condensed:

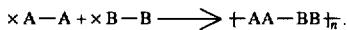

Where the rigid-rod macromonomers are used in a condensation polymerization, the reactive side groups can be considered to be the A-, or B- type end groups typically described in A-A, A-B, and B-B monomers used in condensation polymerization systems. A-A, B-B, and A-B type monomers are described in U.S. Pat. No. 4,000,187 to Stille, incorporated herein by this reference.

Non-limiting examples of A-A and B-B type monomers include diamine-type monomers such as p-phenylenediamine, m-phenylenediamine, oxydianiline, methylenedianiline, tetramethylenediamine, hexamethylenediamine, and the like; diol-type monomers such as resorcinol and hexanediol; bisaminoketones, bisthiols, and the like; diacid-type monomers such as adipic acid, adipoyl chloride, esters of adipic acid, terephthalic acid, terephthaloyl chloride, esters of terephthalic acid, bisketomethylenes, bis(activated halides) such as chlorophenyl sulfone, and the like.

Non-limiting examples of A-B type monomers include amino acids, amino acid esters, activated halides such as 4-fluoro-4'-hydroxybenzophenone, lactams (e.g., caprolactam), lactones, and the like.

Several types of reinforced polymers and copolymers are possible with the rigid-rod macromonomers of the present invention. One skilled in the art will appreciate that the backbone of the macromonomers of the present invention, generally designated "M" can have A-type, B-type, or both A- and B-type reactive side groups pendant therefrom. In other words, a given macromonomer can have reactive side groups that are complementary to A-type, B-type, and/or both A- and B-type condensation monomers.

Figure 2:
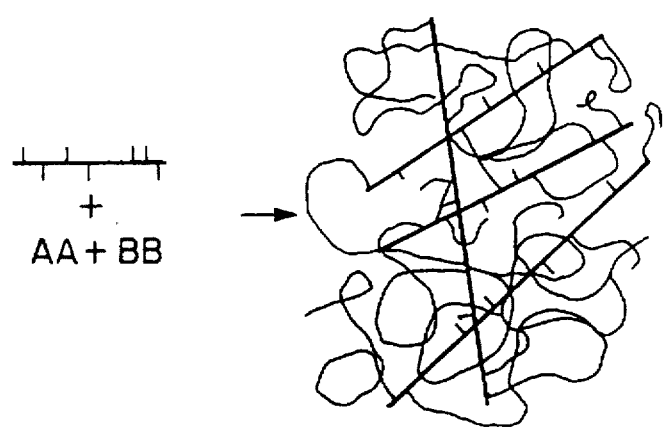
FIG. 2 is a schematic illustration of the formation of a crosslinked polymer prepared by polymerizing macromonomers of the present invention with two different species of complementary monomers.
Figure 3:
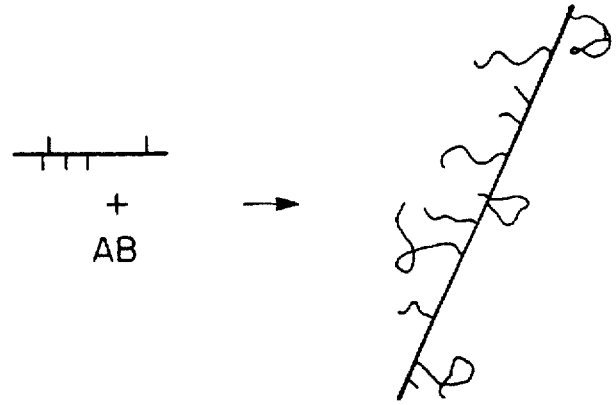
FIG. 3 is a schematic illustration of the formation of a graft polymer formed with macromonomers of the present invention.
Figure 4:
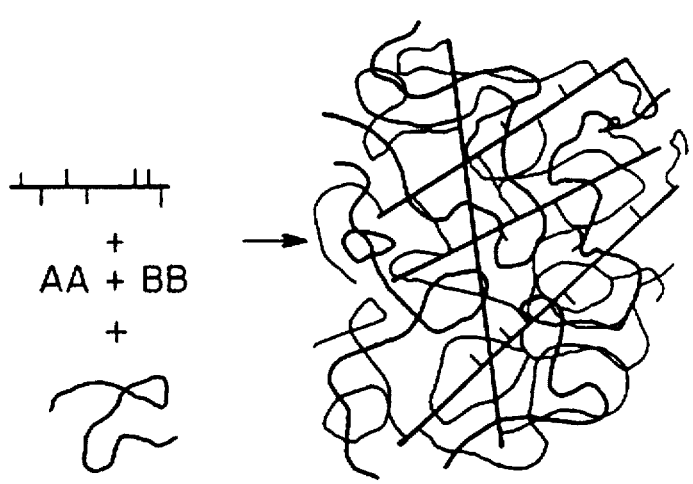
FIG. 4 is a schematic illustration of the formation of a semi-interpenetrating network of an uncrosslinked flexible polymer in a network of a crosslinked monomer/macromonomer system.

Macromonomers having "A" type reactive side groups, complementary to B-B and A-B type condensation monomers, may be used in the following exemplary, and non-limiting, ways:

(a) Macromonomer+AA or BB→crosslinked polymer with short chains between crosslinks (FIG. 1);

(b) Macromonomer+AA+BB→crosslinked polymer with long chains between crosslinks; chain length between crosslinks is dependent on the amounts of A-A and B-B monomers (FIG. 2);

(c) Macromonomer+AB→flexible polymer chains grafted to rigid-rod segments (FIG. 3);

(d) Macromonomers+AA+BB+preformed flexible polymer→semi-interpenetrating network of uncrosslinked flexible polymer in a crosslinked macromonomer–AA–BB network (FIG. 4).

Order of addition and control of monomer imbalance can be used to create complex, crosslinked polymeric compositions. Any set of A-A, B-B and A-B monomers which will co-condense with the macromonomers of the present invention will be called complementary monomers. For example, terephthalic acid and ethylene glycol are complementary monomers that will condense with rigid-rod macromonomers having A-type reactive side groups (for example hydroxyalkyl or carboxylate side groups). Similarly, a copolyester can be formed by condensing A-type macromonomers having structure (1) or (2) with one or more complementary monomers such as biscarboxylic acids, biscarboxylic acid halides, biscarboxylic acid esters, bisdiols, hydroxycarboxylic acids, lactones, and the like.

Three variables which may be used to control the properties of the copolymers prepared by incorporating the macromonomers of the present invention are: the average length of the rigid segments, $L_r$, which is proportional to $DP_n$, the average number of reactive side groups per macromonomer, and the weight fraction of rigid segments in the copolymer, $W_r$.

Reinforcing Thermoset Resins

The rigid-rod macromonomers of the present invention may also be used to form thermoset resins, either alone or in conjunction with existing thermoset formulas to impart strength, stiffness, and/or a lower coefficient of thermal expansion. Thermosets are often formed in stages, where monomers are allowed to react to a limited extent to give a processable resin, which is cured in a second stage, often by heat treatment. Thermosets formed in accordance with the present invention are typically highly crosslinked, and the stages are defined by the degree of crosslinking. Aside from the insoluble, infusible nature of the resulting cured thermoset, the chemistry is similar to condensation polymers.

It will often be desirable to use the rigid-rod macromonomers of the present invention with other small molecule crosslinkers, curing agents, additives, fillers, modifiers and the like. Diols, polyols, diamines and polyamines are commonly used thermoset precursors that will react with the macromonomers of the present invention. A non-limiting example of the use of such compounds is the formation of a two part thermosetting resin, wherein Part 1 is primarily comprised of a rigid-rod macromonomer, and Part 2 is primarily comprised of a curing agent such as a diamine, or a catalyst. Two part resins often have longer shelf lives, because each component alone is relatively unreactive.

Rigid-rod polymers heretofore have not been used in thermosets, primarily because it is commonly thought that rigid-rod polymers are not soluble in resin systems, including solutions of resins or pre-polymers used to prepare thermoset resins. The rigid-rod macromonomers of this invention, however, are soluble in common solvents and can be made compatible with various resin systems by proper choice of solubilizing side groups. The reactive side groups also should be compatible with the cure chemistry of the thermoset.

Typically, but not necessarily, the reactive side groups will be chosen to match the reactive groups in the thermoset. For example, reactive side groups should be epoxy groups, phenol groups, or amino groups for use with an epoxy resin, or phenol groups for use with phenolic resins. It is also usually desirable for the cure temperatures of the reactive side groups and the thermoset to be similar. Non-limiting examples of thermoset systems which can incorporate the rigid-rod macromonomers of present invention are: allyl resins, benzophenonetetracarboxylic acid or its anhydride, bisacetylene resins, bisbenzocyclobutene resins, bisbiphenylene resins, bisphenoltetracarboxylic acid, or its anhydride, diepoxides, epoxy resins, formaldehyde, paraformaldehyde, paraformaldehyde-based resins, furan resins, phenolic resins, polyepoxides, trioxanes, phenol-formaldehyde resins, novolac resins, resole resins, resorcinol-formaldehyde resins, silicone resins, urethanes, melamine resins, isocyanate resins, resins based on cyanuric acid and cyanuric chloride, polyamic acids, polyamide resins, crosslinked polyamides and polyesters, unsaturated polyester resins, urea resins, vinyl ester resins, and natural resins, gums, lacquers and varnishes.

The rigid-rod macromonomers of the present invention may also be used alone to form thermosetting resins. In this case, the side groups G are not needed for solubility in, or compatibility with, other resins, polymers or monomers, but impart some degree of thermoformability. In general, rigid-rod macromonomers with a lower degree of polymerization, smaller n will have lower glass transition temperatures and melting temperatures and will be more readily heat processed. As is known in the art it is necessary to adjust the melting temperature and cure temperature so that the polymer system does not cure before it is thermoformed, and so that unreasonably high temperatures are not needed for curing.

When used as a thermoset, the rigid-rod macromonomer must have sufficient flow properties to be shaped or processed, typically at elevated temperatures. Thus, the side groups G and the $DP_n$ are chosen to allow some degree of thermoformability. In general, larger and more flexible G's increase processability, as does lower $DP_n$. On the other hand, smaller G's and larger $DP_n$'s enhance stiffness and strength, so that optimum sizes for $DP_n$ and G can be found. Different processing methods will have different requirements; for example, sintering does not require complete melting, whereas injection molding requires low viscosity melts. The reactive side groups of a rigid-rod macromonomer used as a thermoset should have a cure temperature consistent with the required processing temperature. If the cure temperature is too low, the material will cure before processing can be completed. If the cure temperature is too high, the material may not fully cure or the flow properties at the curing temperature may be undesirable. In an exemplary and non-limiting embodiment of the invention, cure is effected by using a curing agent such as a catalyst or low molecular weight crosslinking agent.

Non-limiting examples of reactive side groups with good cure temperatures are maleimides, nadimides, and acetylenes.

Reinforcing Addition Polymers

The rigid-rod macromonomers of the present invention also find use as pre- and post-polymerization additives. As post-polymerization additives, rigid-rod macromonomers may be used in compounding, blending, alloying, or otherwise mixing with preformed polymers, preformed blends, alloys, or mixtures of polymers. In these cases the solubilizing side groups and/or reactive side groups help make the macromonomer compatible with the polymer to be reinforced. Such compounding, blending, alloying etc. may be done by solution methods, melt processing, milling, calendaring, grinding or other physical or mechanical methods, or by a combination of such methods. Chemical reaction of the reactive side groups of the macromonomer with the polymer into which the macromonomer is being incorporated may take place during such processes, or the reactive side group may simply serve to make the rigid segment M compatible with the preformed polymer, for example via non-covalent interactions including hydrogen bonding, ionic bonding and van der Waals forces. Mechanical heating or shearing can initiate such chemical processes which will effect the final composition.

Figure 5:
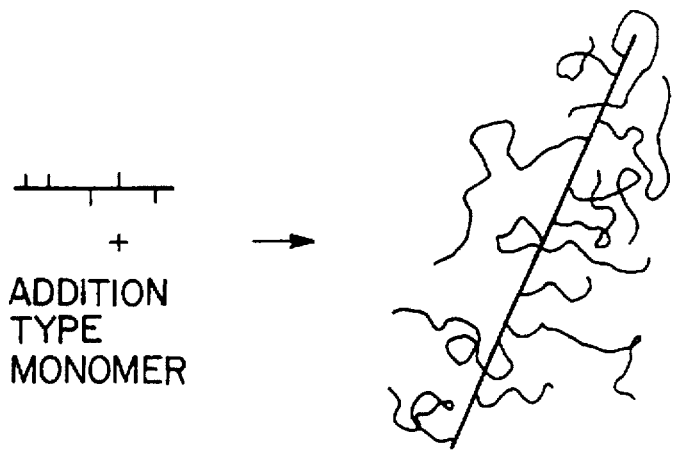
FIG. 5 is a schematic illustration of the formation of a graft copolymer formed with macromonomers of the present invention wherein the reactive side groups are polymerization initiators.

For many addition polymers, where it is not convenient to introduce the macromonomer during polymerization, the rigid-rod macromonomer may be introduced by the above methods in post-polymerization processes. Non-limiting examples of such polymers include, polyethylene, polypropylene, polyvinylchloride, polystyrene, polyacrylonitrile, polyacrylates, acrylonitrile-butadiene-styrene (ABS), styrene butadiene rubber (SBR), and other homopolymers, copolymers, blends, alloys etc. A macromonomer having reactive side groups that act as initiators for addition polymerization can be used to prepare graft copolymers having a rigid-rod main chain and flexible side chains (FIG. 5).

Figure 6:
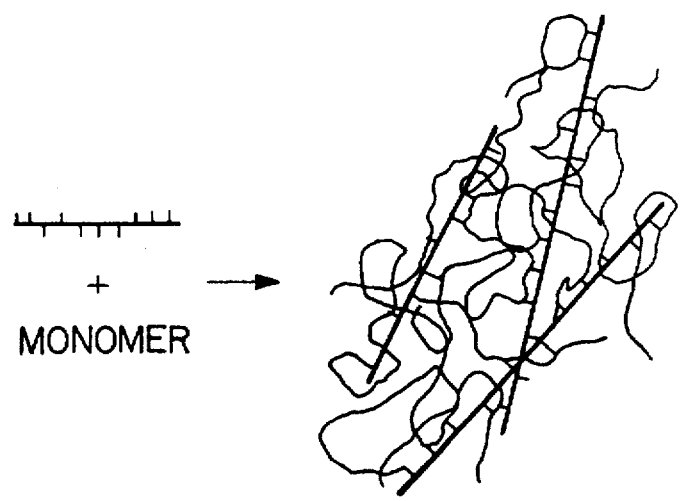
FIG. 6 is a schematic illustration of the formation of a crosslinked polymeric material made with macromonomers of the present invention wherein the reactive side groups can participate in addition type polymerization.

A macromonomer having reactive side groups that act as addition type monomers, for example styrene side groups, may be used to form addition polymers having rigid-rod segments (FIG. 6). Depending on concentrations and reactivity of reactants, the resulting addition polymers will exhibit varying degrees of crosslinking.

The rigid rod macromonomers of the present invention may be used in any of the various types of polymerization processes, including but not limited to, bulk polymerization, suspension polymerization, emulsion polymerization, reaction injection molding, reinforced reaction injection molding, resin transfer molding and the like.

Other applications will be apparent to those skilled in the art.

As pre-polymerization additives, the macromonomers of the present invention are added along with other monomers to be polymerized to yield the final polymer.

Optionally, conventional fillers such as carbon black, silica, talc, powders, chopped or continuous fibers, or other macroscopic reinforcing agents as are known in the art can be added to the polymer systems which incorporate the rigid-rod macromonomers of the present invention. In embodiments of the invention in which macroscopic reinforcing agents are added, the macromonomers of the present invention add additional strength, stiffness, creep resistance, fire resistance toughness and/or other properties to what would otherwise be conventional composites and resins and also serve to decrease the amount of filler used in a conventional composite or resin.

The rigid red macromonomers of the present invention may be used to enhance the properties of all types of natural and synthetic polymers, including but not limited to, addition polymers, condensation polymers, ring opening polymers, thermosets, thermoplastics, elastomers, rubbers, silicones, silicone rubbers, latexes, gums, varnishes, and cellulose derived polymers.

When used with rubbers and elastomers having a polymer network the rigid rod macromonomers act to modify such properties as strength, abrasion resistance, resilience, wear resistance, creep and the like, and may be used to replace or eliminate the use of fillers.

The reinforced polymers of the present invention may be used to fabricate films, fibers, and molded parts having improved properties, especially improved mechanical properties, relative to the same material without reinforcement by rigid-rod macromonomers. Other non-limiting examples of applications of the reinforced polymers of the present invention include adhesives, elastomers, coatings, membranes, plastic sheet, and sheet molding compounds.

The reinforced polymers of the present invention may contain in addition to rigid-rod segments conventional additives, including but not limited to, plasticizers, flame retardants, smoke supressants, fillers, additional polymers, compatibilizers, lubricants, surface modifiers, antioxidants, dyes and pigments, surfactants, biodegradability enhancers, biomodifiers, UV absorbers and the like.

Methods for Preparing Macromonomers Having Reactive Side Groups

In order to introduce rigid segments into a wide variety of polymers, polymeric compositions, ceramics, glasses, and the like, a rigid-rod type macromonomer is first prepared. The poly-1,4-phenylene structure (1) and aza derivatives (structure (2)) offer a stiff, strong, thermally stable and chemically inert backbone, of potentially low cost. Pendent side groups impart solubility and reactivity to the macromonomer.

Several methods may be used to prepare substituted poly-para-phenylenes and aza analogs. The simplest rely on reductive condensation of 1,4-dihaloaromatics, either by way of a Grignard reagent, or directly. A catalyst, such as bis(triphenylphosphine) nickel (II) chloride or 1,4-dichloro-2-butene is used. Para-bromoaryl boronic acids may be coupled using palladium based catalysts. Polyphenylenes have also been prepared by methods which do not give exclusive para linkage, such as Diels-Alder condensation of bis-acetylenes and bis-pyrones, polymerization of 1,3-cyclohexadiene followed by aromatization and oxidative polymerization of benzene.

If the macromonomer is prepared using a transition metal catalyst, and the synthesis proceeds through metallo-terminated chains as intermediates, the molecular weight of the resulting macromonomer may be controlled by the catalyst-to-monomer ratio. In this case the polymerization will cease when the number of chain ends (capped with catalyst) equals the number of catalyst molecules initially present. The $DP_n$ will equal twice the monomer to catalyst ratio. End groups (not shown in the structures provided herein) then may be introduced by adding reagents which displace the metallo end groups. For example, if the macromonomer is worked-up in an alcohol, the metal groups terminating the chains of the macromonomer are displaced by protons (H). The metallo-terminated macromonomer is thereby quenched.

Macromonomers of the present invention may have, in addition to reactive side groups, reactive end groups. Macromonomers having reactive end groups may be prepared, for example, by adding endcappers during the coupling reaction, or by displacing the metallo end groups with an endcapper. The endcappers may themselves be reactive groups or protected forms of reactive groups.

The rigid-rod macromonomers of the present invention may be made by these and other methods, keeping in mind the special requirements of solubilizing and reactive side groups. The catalytic reductive coupling of 1,4-dihaloaryls is preferred, (and more preferably, reductive coupling of 1,4-dichloroaryls) because of its simplicity and wider tolerance of functional groups. The special nature of the rigid-rod macromonomers of the present invention must be taken into account in order to successfully prepare these macromonomers.

Rigid-rod macromonomers comprised of both monomer units bearing solubilizing side groups and monomer units bearing reactive side groups are conveniently prepared by either of two different routes. One approach is to copolymerize two or more different monomers, at least one of which bears one or more reactive side groups. A non-limiting example is copolymerization of a 19:1 molar ratio of 2,5-dichlorobenzophenone and methyl-2,5-dichlorobenzoate to yield a macromonomer having a structure (4):

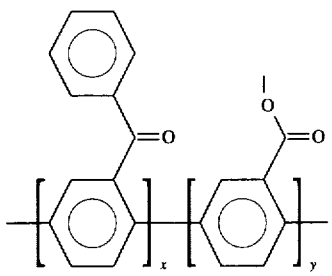

(4)

where x≈95%, y≈5% and the monomer units bearing a reactive ester group are randomly distributed amongst the monomer units bearing a solubilizing benzoyl group.

A second approach is to first prepare a homopolymer and then react an excess of said homopolymer with a predetermined amount of a reagent to yield a partially modified polymer that is, in effect, a copolymer. A non-limiting example is polymerization of 2,5-dichlorobenzophenone to yield parapolybenzoylphenylene, followed by treatment with a predetermined amount of methyl lithium, followed by hydrolysis to yield a macromonomer having the structure (5):

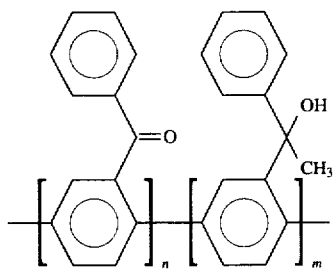

(5)

where n+m=100%, and the monomer units bearing a reactive benzylhydroxy side group are randomly distributed amongst the monomer units bearing a solubilizing benzoyl group.

A second non-limiting example of side chain modification is the treatment of parapolybenzoylphenylene with a predetermined amount of phenol in the presence of a Lewis acid catalyst to give a macromonomer having the structure (6):

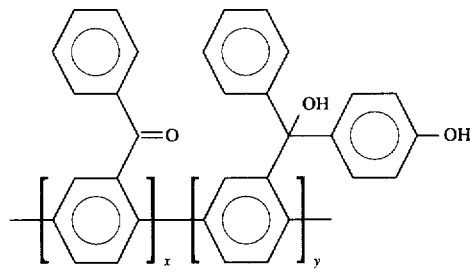

where x+y=100%, and the monomer units bearing a reactive (and solubilizing) phenolic side group are randomly distributed amongst the monomer units bearing a solubilizing benzoyl group.

The synthesis of even short rigid-rod molecules is made difficult by their low solubility. For example, poly-1,4-phenylene (structure (1), where $G_1$ through $G_4$ and E are each hydrogen) compounds with n greater than about 8 are essentially insoluble in all solvents and are infusible. Solubility is achieved in the present invention by appropriate choice of side groups G, bearing in mind the solvent systems to be employed. For example, for polar aprotic solvents, such as dimethylformamide or N-methylpyrrolidone, polar aprotic side groups such as amides and ketones are appropriate. For protic solvents, e.g. water, acids or alcohols, ionizable side groups, e.g. pyridyl or sulfonate, might be considered.

The side groups may also act to twist the main chain phenylene units out of planarity (although the main chain remains straight and not coiled). Phenylene pairs with substituents at the 2,2' positions will be twisted out of planarity by steric repulsion. Since planar phenylene chains pack more efficiently, a twisted chain will be more soluble. One means of solubilizing rigid-rod molecules is to provide adjacent phenylene pairs with substituents ortho with respect to the other phenylene of the pair. Even occasional 2,2' side groups will disrupt packing and enhance solubility. Another means of improving solubility is to decrease the order (increase the entropy) of the side groups, for example by a random copolymer with two or more different types of substituents. Other mechanisms of increasing solubility may also be possible.

Non-limiting examples of solubilizing side groups are: phenyl, biphenyl, naphthyl, phenanthryl, anthracenyl, benzyl, benzoyl, naphthoyl, phenoxy, phenoxyphenyl, phenoxybenzoyl, alkyl, alkyl ketone, aryl, aryl ketone, aralkyl, alkaryl, alkoxy, aryloxy, alkyl ester, aryl ester (esters may be C-bound or O-bound), amide, alkyl amide, dialkyl amide, aryl amide, diaryl amide, alkyl aryl amide, amides of cyclic amines such as piperidine, piperazine and morpholine (amides may be CO-bound or N-bound), alkyl ether, aryl ether, alkyl sulfides, aryl sulfides, alkyl sulfones, aryl sulfones, thioethers, fluoro, trifluoromethyl, perfluoroalkyl, and pyridyl, where alkyl is a linear or branched hydrocarbon chain having between 1 and 30 carbon atoms, and aryl is any single, multiple or fused ring aromatic or heteroaromatic group having between 3 and 30 carbon atoms. Fluorine-substituted analogs of the above-identified side groups may also be used.

$G_1$ and $G_2$, and/or $G_3$ and $G_4$ may be interconnected to form bridging groups. Non-limiting examples of such groups and the monomer units that result are shown below:

$G_1$    $G_2$    Resulting Monomer Unit

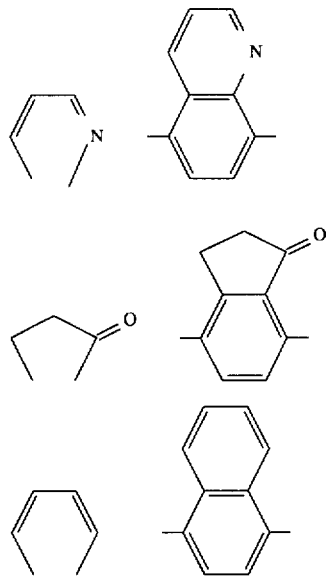

Solubilizing side groups G may also be oligomeric or polymeric groups. Using side groups which are functionally equivalent to the flexible polymer to be strengthened increases the compatibility of the rigid segments with the flexible segments. A non-limiting example is the use of a macromonomer denoted "$M_{oligo}$," bearing oligocaprolactam side groups G, as a comonomer with caprolactam in the preparation of poly(hexamethyleneadipamide-co-$M_{oligo}$).

For cases where the monomer unit of the macromonomer is unsymmetrical about the plane perpendicular to the polymer axis and centered on the monomer unit, for example if $G_1$ is benzoyl and $G_2$, $G_3$, and $G_4$ are hydrogen, isomeric forms of the macromonomer exist. The monomers can link exclusively head-to-tail to form a regular structure. The monomers can also form a regular structure by linking exclusively head-to-head and tail-to-tail. Other more complicated structures and a random structure are also possible. The particular monomers and conditions used to form the macromonomer will determine the detailed structure. As used herein, structures (1), (2) and (3) represent all isomeric cases, either regular or random. Similarly, macromonomers of the type depicted in structures (4)–(6) are not limited to the particular isomers shown therein.

It will sometimes be desirable to include 1,4-dichlorobenzene as a comonomer, so that some monomer units will be unsubstituted, i.e., $G_1=G_2=G_3=G_4=H$. The unsubstituted units will lower cost, but may also lower solubility.

Reactive Side Groups

The reactive side groups, G, are chosen to allow chemical interaction with the flexible polymer or inorganic matrix to be stiffened or strengthened.

Reactive side groups can be further derivatized to provide additional functionality, as for example during deprotection, or transformation of one reactive group into another, for example reduction of a nitrile into an amine, an aldehyde into an alcohol, or conversion of an amine into an imine. More than one type of reactive side group may be present.

Amines form an important class of reactive side groups. Amine-functionalized macromonomers can be used with polyamides, polyimides, polyimidamides, polyureas, polyimines, and other polymers derived from bisamine monomers. Amine-functionalized macromonomers can also be used with polymers not derived from bisamine monomers, such as epoxides and polyesters; in the latter case the macromonomer would be incorporated into the polyester chain via amide links. Preparation of the amine-functionalized macromonomers can involve protection/ deprotection of the amine groups, for example as a succinimide or an amide.

The following are-non-limiting examples of amine derived reactive side groups: amino, aminoalkyl, aminoaryl, aminoalkaryl, aminoaralkyl, aniline, C-alkylaniline, N-alkylaniline, aminophenoxy, and aminobenzoyl. Other substituted and/or chemically protected aniline side groups may also be used. The following structures illustrate non-limiting examples of amine-derived reactive side groups. Typical amines, amino alkyls, and amino aralkyls are given by the following structures (7a–7c):

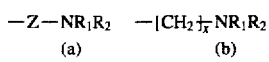
(a)  (b)  (7a–7c)

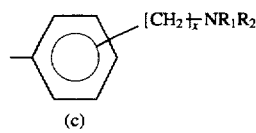
(c)

where $R_1$ and $R_2$ may be independently chosen from: hydrogen, alkyl, aryl, alkaryl, aralkyl, alkylketone, arylketone, alkylether or arylether, where alkyl and aryl are as defined above, x ranges from one to about twenty and Z is a difunctional group chosen from: nil, phenyleneoxy, ketophenylene, phenylenesulfone, —O—, —NH—, keto, —SO₂—, aryl, alkyl, alkaryl, or aralkyl. $R_1$ and $R_2$ include bridging groups, such as —CH₂CH₂CH₂CH₂CH₂—, —CH₂CH₂OCH₂CH₂—, and —CH₂CH₂CH₂CO—. $R_1$ and $R_2$ will often be used as protecting groups, to be removed at a later stage of processing, and as such include common amine and alcohol protecting groups, non-limiting examples of which are: trimethylsilyl, trityl, tetrahydropyranyl tosyl methoxyisopropylidene, imide, imine, amide, ester, and the like.

Typical amino aryl reactive side groups, G, have the structures (8a–8c):

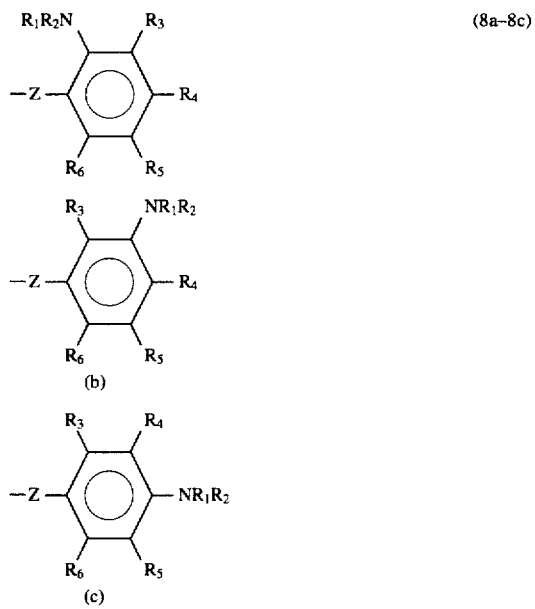
(8a–8c)
(b)
(c)

where Z, $R_1$ and $R_2$ are as defined above, and $R_3$–$R_6$ are selected from the same group as $R_1$ and $R_2$. Aniline side groups have the above structure where Z is nil and the R's are all hydrogen.

Aminophenoxyphenyl and aminobenzophenone side groups have the general structures (9a and 9b):

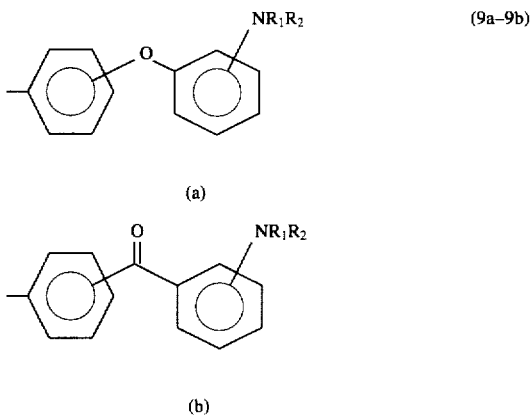
(9a–9b)
(a)
(b)

where $R_1$ and $R_2$ are as defined above.

Imides comprise a second class of reactive side groups. The maleimides are represented by the structures 7a–9b, where $R_1$ and $R_2$ together equal the bridging group —COCH═CHCO—. Bismaleimides are commercially valuable in thermoset resins. Rigid-rod macromonomers with maleimide end groups are useful for strengthening conventional bismaleimide resins. They may also be used alone as novel bismaleimide resins containing rigid-rod elements. Other reactive imide end groups are contemplated by the present invention, including the nadimide end groups. Unreactive imides may also be used; succinimide may be used as a protected form of amine.

Closely related to the amines are the amides. In structures 7a–9b, if $R_1$ or $R_2$═—COalkyl or —COaryl, the reactive side groups are amides. If $R_1$ or $R_2$═—COCH═CH$_2$, the reactive side groups are acrylamides. Amide-functionalized macromonomers are also useful in reinforcing polyamides, such as nylon. Amide groups may react by transamination with the flexible polymer during polymerization or compounding.

Another important class of reactive side groups are alcohols and ethers. Diol-functionalized macromonomers may be used as comonomers with other diol monomers. Polyesters, polycarbonates, urethanes, and polyethers are non-limiting examples of polymers prepared from diols. Alcohol macromonomers may also be used in non-diol derived polymers, for example, polyamides, where linkage to the macromonomer is through ester links. Both the amine macromonomers and the alcohol macromonomers may be used to replace dibasic monomers, in general, in condensation polymerizations.

Non-limiting examples of alcohol-functionalized macromonomers are: hydroxy, hydroxyalkyl, hydroxyaryl, hydroxyalkaryl, hydroxyaralkyl, phenol, C-alkylphenol, O-alkylphenol, hydroxyphenoxy, and hydroxybenzoyl. The following non-limiting structures (10a–10c) illustrate exemplary alcohol side groups:

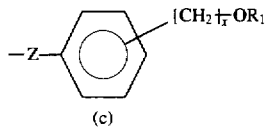

where $R_1$, x and Z are as defined in the discussion following structures (7a–7c).

The following structures (11a–11c) are representative of phenolic side groups:

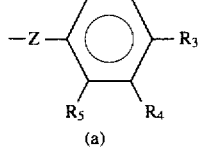

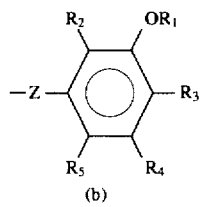

where $R_1$–$R_6$, and Z are as defined above.

The following structures (12a–12c) are more specific examples of the above structures:

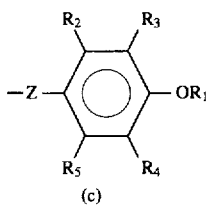

where $R_1$ is as defined above.

For $R_1$=H, the structures (12a–12c) represent phenol, hydroxyphenoxyphenyl, and hydroxybenzophenone side groups, respectively. For $R_1$=ketoalkyl or ketoaryl, the structures (12a–12c) are phenylesters. $R_1$ may contain additional reactive groups, such as acrylate or vinyl. In structures 9a through 11c, for $R_1$═—COCH═CH$_2$ the reactive side groups are acrylates, for $R_1$═—CH═CH$_2$ the reactive side groups are vinyl ethers.

Carbonyl-containing reactive side groups including acetyl, formyl, carboxy, ester, amide, acrylate, ketoalkyl and ketoaryl are represented by the structures (12a–12d) where Y is CH$_3$, H, OH, OR$_1$, NR$_1$R$_2$, vinyl, alkyl and aryl respectively, and $R_1$–$R_6$ and Z are as defined above. Amides may be C or N bound; see structures 6a–8b above.

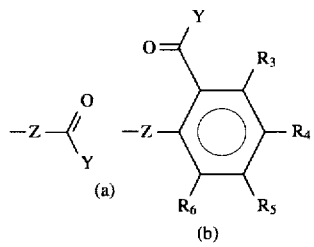

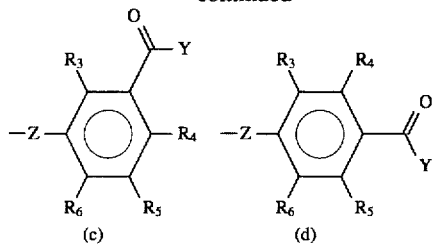

Macromonomers of the present invention having carboxy side groups may be used to reinforce polyesters and polyamides.

Acetylene side groups have the structures (14a–14d) where Y is —CCH. Olefin side groups have the structures (14a–14d) where Y is —CH=CH$_2$. Halide, cyano, cyanate, and isocyanate side groups have the structures (14a–14d) where Y is -halogen, —CN, —OCN and —NCO respectively.

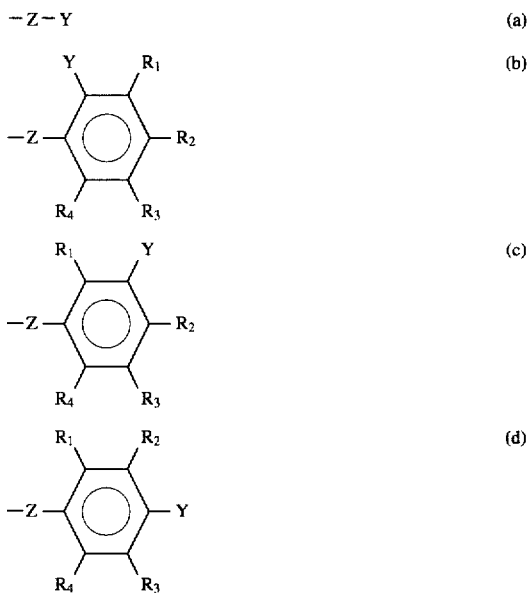

Reactive side groups may also be strained ring compounds including epoxides, biphenylenes and benzocyclobutenes.

In situations where the reactive side groups G are reactive with each other, both the reactive side groups G and the groups on the flexible polymer or monomer which they are ultimately to react should be selected so that the relative rates of reaction are approximately equal. This will enhance the randomness of the distribution of the macromonomer within the final polymer.

When the rigid-rod macromonomers of the present invention are used as pre-polymerization additives, they are preferably added in an amount such that $W_r$ ranges from 1 percent to 60 percent, i.e., the rigid-rod macromonomers make up from 1 percent to 60 percent of the weight of the resulting polymeric material. Such a range takes into account the trade off between increased cost and decreased processibility that results as the value of $W_r$ increases in magnitude. In practice, it is desirable to experimentally determine the optimal weight fraction required for particular applications.

In certain circumstances, it may be desirable for $W_r$ to exceed 60 percent of the total weight of the copolymeric material. For instance, when the rigid-rod macromonomers of the present invention are used alone as thermosetting resins, $W_r$ can approach the limiting value of 100 percent, depending on the size, frequency, and orientation of the crosslinking groups formed during curing.

There will also be an optimal range for $L_r$, typically between 8 and 500 repeat units, beyond which additional increases in length will have little further effect on strength or stiffness but will reduce processibility. Optimal ranges for both $W_r$ and $L_r$ can be readily determined by one skilled in the art.

The aspect ratio of the macromonomers incorporated into copolymers also affects the physical properties of the copolymers, particularly the processibility thereof. The aspect ratio of a macromonomer is defined to be the length to diameter ratio of the smallest diameter cylinder which will enclose the macromonomer segment, including half the length of the terminal connecting bonds, including hydrogen but not any other attached side groups, such that the axis of the cylinder is parallel to the connecting bonds in the straight segment.

For rigid-rod polyphenylenes, and aza analogs, the aspect ratio is approximately equal to the $DP_n$, because the phenylene monomer unit has an aspect ratio of about one.

When the average aspect ratio of the macromonomers is less than about 7 or 8, the macromonomers typically do not impart the desired strength and stiffness into the final polymer. As the aspect ratio is increased, the mechanical properties of the reinforced polymer improve. All other factors being equal, a longer rigid segment will provide a greater increase in stiffness than a shorter rigid segment. This is true for reinforcement of any geometrical type of polymer, e.g., linear, branched, crosslinked, and the like. It is known in the art that for conventional fiber-containing composites mechanical properties improve rapidly up to aspect ratios of about 100, after which there are lesser improvements. A similar situation has been found to exist for rigid-rod macromonomers.

Although mechanical properties of the polymers improve as the aspect ratio increases, processing becomes more difficult. Viscosities of polymer solutions are dependent on the $DP_n$ of the polymer. Viscosities of rigid-rod polymers increase much more rapidly with $DP_n$ than viscosities of flexible polymers. Similarly, melt viscosities of flexible polymers reinforced with rigid-rod polymers increase with the $DP_n$ of the rigid segments, making thermal processing more difficult as $DP_n$ increases.

There is generally a trade-off between improved mechanical properties and difficulty of processing, resulting in an optimal aspect ratio and $DP_n$ for the rigid-rod macromonomers. For example, if it is desired to increase the modulus of a flexible polymer reinforced with rigid-rod macromonomers, the aspect ratio of the macromonomer could be increased, but the melt and solution viscosity will increase and solubility of the rigid-rod macromonomer will decrease, making processing and preparation more difficult. $DP_n$'s of about 100 are often optimal; however, higher or lower $DP_n$'s may sometimes be desirable.

SYNTHETIC METHODS

The following synthetic procedures are exemplary methods that may be used in the preparation of precursors to, and reagents used in the synthesis of, the rigid-rod macromonomers of the present invention; an exemplary method of preparing succinimide-protected amines; and a method for deprotecting protected side groups. The choices and amounts of reagents, temperatures, reaction times, and other parameters are illustrative but are not considered limiting in any way. Other approaches are contemplated by, and within the scope of, the present invention.

Preparation of 2,5-Dichlorobenzoyl Compounds 2,5-dichlorobenzoyl-containing compounds (e.g. 2,5-dichlorobenzophenones and 2,5-dichlorobenzamides) can be readily prepared from 2,5 dichlorobenzoylchloride. Pure 2,5-dichlorobenzoylchloride is obtained by vacuum distillation of the mixture obtained from the reaction of commercially available 2,5-dichlorobenzoic acid with a slight excess of thionyl chloride in refluxing toluene. 2,5-dichlorobenzophenones (2,5-dichlorobenzophenone, 2,5-dichloro-4'-methylbenzophenone, 2,5-dichloro-4'-methoxybenzophenone, and 2,5-dichloro-4'-phenoxybenzophenone) are prepared by the Friedel-Crafts benzoylations of benzene and substituted benzenes (e.g. toluene, anisole, diphenyl ether, respectively), with 2,5-dichlorobenzoylchloride at 0°–5° C. using 2–3 mole equivalents of aluminum chloride as a catalyst. The solid products obtained upon quenching with water are purified by recrystallization from toluene/hexanes. 2,5-dichlorobenzoylmorpholine and 2,5-dichlorobenzoylpiperidine are prepared from the reaction of 2,5-dichlorobenzoylchloride and either morpholine or piperidine, respectively, in toluene with pyridine added to trap the HCl that is evolved. After washing away the pyridinium salt and any excess amine, the product is crystallized from the toluene solution.

Preparation of Activated Zinc Powder

Activated zinc powder is obtained after 2–3 washings of commercially available 325 mesh zinc dust with 1 molar hydrochloric acid in diethyl ether (anhydrous) and drying in vacuo or under inert atmosphere for several hours at abut 100°–120° C. This material should be used immediately or stored under an inert atmosphere away from oxygen and moisture.

Preparation of Succinimide Protected Amines

The dry amine (0.5 mole) and succinic anhydride (0.5 mole) are dissolved in 2 L dry toluene. Catalyst, p-toluenesulfonic acid (0.01 mole), is then added and the mixture is held at reflux for 24 hours, using a Dean-Stark trap to collect water. After cooling, the product is precipitated with diethyl ether, filtered, washed with ether and dried.

Deprotection of Protected Side Groups

In the cases where the functional side groups are protected as an imide, amide, or ester, the protecting groups are removed as follows: The protected macromonomer is suspended in 25 ml of 10% HCl in ethanol and heated to reflux for six to twelve hours. This mixture is neutralized with sodium hydroxide, filtered, washed and dried. Further purification by dissolution and precipitation by adding a nonsolvent may be effected.

The following specific examples of preparing rigid-rod macromonomers and polymers containing rigid-rod macromonomers are illustrative-of the present invention, but are not considered limiting thereof in any way.

EXAMPLE 1

Preparation of a macromonomer of the structure

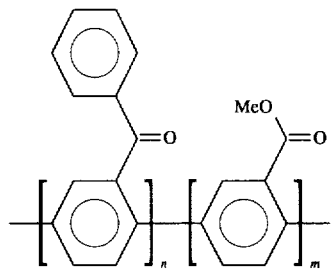

Anhydrous bis(triphenylphosphine) nickel(II) chloride (0.25 g; 0.39 mmol), triphenylphosphine (0.60 g; 2.29 mmol), sodium iodide (0.175 g, 1.17 mmol) and 325 mesh activated zinc powder (1.2 g; 18.4 mmol) are placed into a flask under an inert atmosphere along with 7 ml of anhydrous N-methylpyrrolidinone (NMP). This mixture is stirred for about 10 minutes at room temperature, leading to a deep-red coloration. A solution of 2,5-dichlorobenzophenone monomer (3.26 g; 12.98 mmol) and of methyl-2,5-dichlorobenzoate comonomer (0.14 g; 0.68 mmol) in 8 ml of anhydrous NMP is then added by syringe. After stirring for about 12 hours at 50°–60° C., the resulting viscous solution is poured into 100 ml of 1 molar hydrochloric acid in ethanol to dissolve the excess zinc metal and to precipitate the functionalized copolymer. This suspension is filtered and the precipitate triturated with acetone and dried to afford a light yellow to white powder. Approximately 5% of the sidechain appendages of the resulting rigid-rod copolymer contain reactive ester groups. Even greater reactivity may be imparted by hydrolyzing the ester groups to carboxy groups (e.g. by refluxing in 10% HCl in ethanol for six to twelve hours and then neutralizing with sodium hydroxide).

EXAMPLE 2

Preparation of a macromonomer of the structure

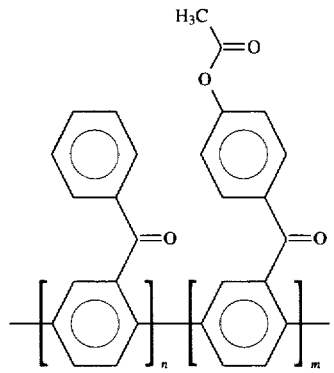

The procedure of Example 1 is followed, where the comonomer is 4'-acetoxy-2,5-dichlorobenzophenone (0.20 g; 0.65 mmol). Approximately 5% of the sidechain appendages of the resulting rigid-rod copolymer contain reactive ester groups. Even greater reactivity may be imparted by hydrolyzing the ester groups to phenolic groups (e.g. by refluxing in 10% HCl in ethanol for six to twelve hours and then neutralizing with sodium hydroxide).

4'-Acetoxy-2,5-dichlorobenzophenone is prepared by treating 4'-Hydroxy-2,5-dichlorobenzophenone, which is prepared by the Friedel-Crafts acylation of phenol with 2,5-dichlorobenzoyl-chloride, with acetyl chloride.

EXAMPLE 3

Preparation of a macromonomer of the structure

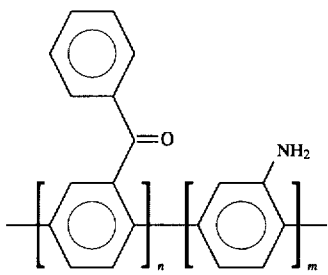

The procedure of Example 1 is followed where the comonomer is 2,5-dichlorophenylsuccinimide (0.17 g; 0.70 mmol). The isolated material is refluxed in 10% HCL in ethanol for six hours and then neutralized with sodium hydroxide. Approximately 5% of the sidechain appendages of the resulting rigid-rod copolymer contain reactive amine groups.

EXAMPLE 4

Preparation of a macromonomer of the structure

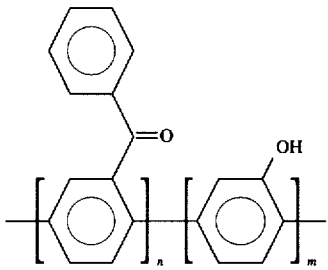

The procedure of Example 1 is followed, where the comonomer is the tetrahydropyranyl ether of 2,5-dichlorophenol (0.17 g; 0.69 mmol). The isolated material is refluxed in 10% HCL in ethanol for six hours and then neutralized with sodium hydroxide. Approximately 5% of the sidechain appendages of the resulting rigid-rod copolymer contain reactive hydroxy groups.

EXAMPLE 5

Preparation of a macromonomer of the structure

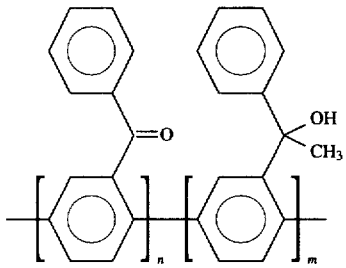

A solution of parapolybenzoylphenylene (0.5 g; 2.8 mmol of monomer units) in 50 ml of diphenyl ether is treated with 0.2 ml (0.28 mmol) of 1.4 molar methyl lithium (ether solution) and heated at 100° C. for 2–3 days. This mixture is poured into 1 molar sulfuric acid in ethanol to hydrolyze the lithio salt and precipitate the product. Approximately 10% of the sidechain appendages of the resulting rigid-rod copolymer contain reactive hydroxy groups.

Parapolybenzoylphenylene is prepared as follows: Anhydrous bis(triphenylphosphine) nickel(II) chloride (0.25 g; 0.39 mmol), triphenylphosphine (0.60 g; 2.29 mmol), sodium iodide (0.175 g; 1.17 mmol), and 325 mesh activated zinc powder (1.3 g; 20 mmol) are placed into a flask under an inert atmosphere along with 7 ml of anhydrous N-methylpyrrolidinone (NMP). This mixture is stirred for about 10 minutes at room temperature, leading to a deep-red coloration. A solution of 2,5-dichlorobenzophenone monomer (4.0 g; 16 mmol) in 8 ml of anhydrous NMP is then added by syringe. After stirring for about 12 hours at 50°–60° C., the resulting viscous solution is poured into 100 ml of 1 molar hydrochloric acid in ethanol to dissolve the excess zinc metal and to precipitate the polymer. This suspension is filtered and the precipitate triturated with acetone and dried to afford a light yellow to white powder.

EXAMPLE 6

Preparation of a macromonomer of the structure

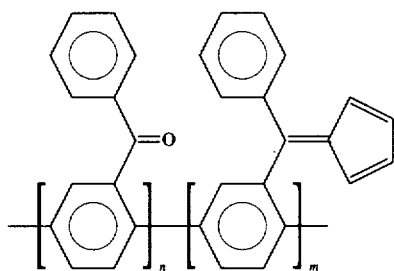

A solution of parapolybenzoylphenylene (1.0 g; 5.6 mmol of monomer units) in 100 ml of diphenyl ether is treated with 0.25 ml (0.5 mmol) of 2 molar sodium cyclopentadienide (tetrahydrofuran solution) and heated at 100° C. for 4 hours. This mixture is poured into 1 molar hydrochloric acid in ethanol to precipitate the product. Approximately 9% of the sidechain appendages of the resulting rigid-rod copolymer contain reactive fulvene groups.

EXAMPLE 7

Preparation of a macromonomer of the structure

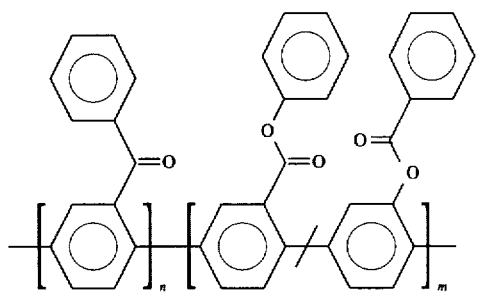

A solution of parapolybenzoylphenylene (0.5 g; 2.8 mmol of monomer units) in 50 ml of methylene chloride is treated with 0.1 g (0.29 mmol) of 50% 3-chloroperoxybenzoic acid (MCPBA) and refluxed for 7 days. This mixture is poured into acetone to precipitate the product. Approximately 10% of the sidechain appendages of the resulting rigid-rod copolymer contain reactive ester groups.

EXAMPLE 8

Preparation of a macromonomer of the structure

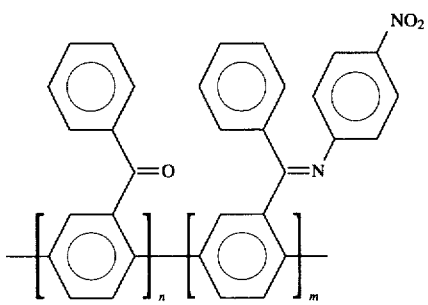

A solution of parapolybenzoylphenylene (0.5 g; 2.8 mmol of monomer units) and 4-nitroaniline (25 mg; 0.18 mmol) in 50 ml of NMP is refluxed for 48 hours. This mixture is poured into ethanol to precipitate the product. Approximately 6.5% of the sidechain appendages of the resulting rigid-rod copolymer contain reactive nitro groups.

EXAMPLE 9

Preparation of a macromonomer of the structure

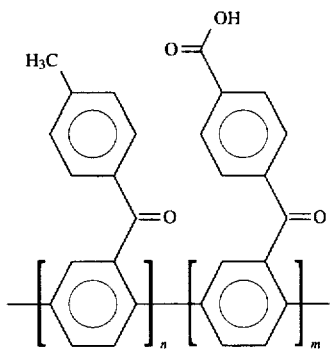

A mixture of parapolytoluoylphenylene (0.5 g; 2.6 mmol of monomer units) and potassium permanganate (0.16 g; 1.0 mmol) in 50 ml of glacial acetic acid is refluxed for 18 hours. This mixture is poured into ethanol, and the product removed by filtration. Approximately 10–20% of the sidechain appendages of the resulting rigid-rod copolymer contain reactive carboxy groups.

Parapolytoluoylphenylene is prepared in the same manner as parapolybenzoylphenylene, except that a solution of 2,5-dichloro-4'-methylbenzophenone monomer in anhydrous NMP is used in place of 2,5-dichlorobenzophenone.

EXAMPLE 10

Preparation of a macromonomer of the structure

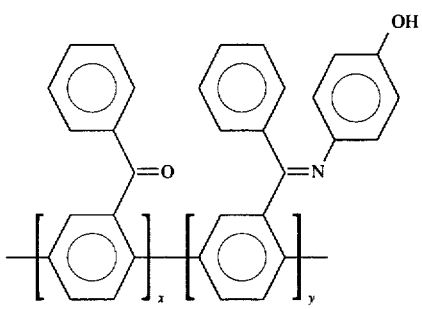

A solution of parapolybenzoylphenylene (500 g; 2.78 mol of monomer units), 4-aminophenol (30 g; 0.278 mol), and p-toluenesulfonic acid monohydrate (1.9 g; 0.01 mol) in chlorobenzene (5 l) is heated to 80° C. for 48 hrs. This mixture is poured into ethanol to precipitate the product. Approximately 10% of the sidechain appendages of the resulting rigid-rod copolymer contain reactive phenol groups.

EXAMPLE 11

Preparation of a nylon-6/polyparaphenylene graft copolymer

The procedure of Kohan for the preparation of poly-ε-caprolactam (Nylon-6) given in *Macromolecular Synthesis*, J. A. Moore, Ed., John Wiley & Sons; New York (1977), Coll. Vol. 1, pp. 91–94 (incorporated herein by this reference), is followed, except that 2.5 g of the ester-functionalized macromonomer of Example 1 is added along with the ε-caprolactam. More specifically, a 38×300 mm Pyrex® test tube fitted with 8 mm Pyrex® inlet and exit tubes is charged with ε-caprolactam (50 g), the ester-functionalized macromonomer of Example 1 (2.5 g), and a 50% by weight aqueous solution of an amine salt as catalyst. The tube is swept with nitrogen for 5 minutes, after which the nitrogen flow rate is adjusted to 350 cc. per minute. The tube is immersed to a depth of 9 inches in a 280°–285° vapor bath. After 4 hours, the test tube is removed from the bath and allowed to cool to room temperature. A polymer plug, which can be cut to a desired particle size, is obtained by breaking the test tube away from the polymer. The polymer can then be extracted. The resulting resin is approximately 5% by weight rigid-rod.

A 50% by weight aqueous solution of an amine salt catalyst is prepared by dissolving or dispersing in water an amine, such as hexamethylenediamine, piperazine, 3,3'(methylimino)bispropylamine, 3,3'-iminobispropylamine, m-xylylene diamine, and the like; dissolving or dispersing in water an acid, such as adipic acid, sebacic acid, and the like; and then slowly adding one solution to the other. Impurities can be removed by treating the resulting solution with Darco G-60, and the filtrate can be used directly as the catalyst. Stoichiometric equivalents of the amine and acid are used, unless the amine is somewhat volatile, in which case a 1% excess of the amine is used. Amino acids are also suitable for preparation of an amine salt catalyst.

EXAMPLE 12

Preparation of an aromatic polyester-derived graft copolymer

In a flamed 500 ml flask equipped with a magnetic stirrer, 9.931 g (43.50 mmol) of bisphenol-A, 8.894 g (43.81 mmol) of isophthaloyl dichloride, 2.362 g (0.62 mmol of phenolic groups) of the phenolic functionalized macromonomer of Example 1, and 15 ml of pyridine in 100 ml of tetrachloroethane are added under nitrogen pressure and heated at 120° C. for 20 hours. The copolymer is precipitated in methanol, filtered, redissolved in chloroform, reprecipitated in methanol, filtered, and dried at 80°–100° C. in vacuo. The resulting graft copolymer is approximately 13% by weight rigid-rod.

EXAMPLE 13

Preparation of an epoxy resin containing a rigid-rod macromonomer

The macromonomer of Example 9 (10 g) is mixed with the diglycidyl ether of bisphenol-A (150 g) (EPON 825, commercially available from Shell Chemical Co.) with warming. After the macromonomer has dissolved to the fullest extent possible, triethylene tetramine (10 g) is added to initiate curing. The resin is applied immediately after adding the curing agent, and is fully cured in 24 hours.

EXAMPLE 14

A macromonomer additive for polyamide modification

The macromonomer of Example 1 (500 g) is blended with polyhexamethylene adipamide (5 kg) in a laboratory scale extruder to form a concentrate. The concentrate is tumble blended with polyhexamethylene adipamide pellets in a 1 to 5 ratio. The mixed pellets are used to fabricate parts via injection molding. The resulting molded objects have approximately 2% rigid-rod macromonomer incorporated by at least partial transamidation-transesterification which occurs during blending and molding.

EXAMPLE 15

Rigid-Rod Macromonomer-reinforced polystyrene

The macromonomer of Example 6 (12 g) is mixed with styrene (150 g) (freed of inhibitor by distillation under reduced pressure) and benzoyl peroxide (3 g) in an evacuable mold. The mold is degassed and sealed under vacuum. The mold is held at 55°–60° C. for 3 days. The mold is cooled, and opened to release the finished part.

EXAMPLE 16

Rigid-Rod Macromonomer-reinforced fiberglass

The macromonomer of Example 6 (100 g) is blended with a general purpose unsaturated polyester resin (5 kg) and methyethylketone peroxide (50 g) catalyst and the resulting mixture is applied to glass fiber matting in a mold, using standard hand lay-up techniques. Peak curing temperature is about 110°–130° C., and curing time is about 30 min.

The above descriptions of exemplary embodiments of macromonomers having functional side groups, the rigid-rod polymers, copolymers, and resins prepared therefrom, and the processes for making same are illustrative of the present invention. Because of the variations which will be apparent to those skilled in the art, however, the present invention is not intended to be limited to the particular embodiments described above. The scope of the invention is defined in the following claims.

What is claimed is:

1. A mixture composition comprising:
   a macromonomer having the structure

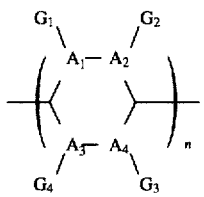

wherein each $A_1$, $A_2$, $A_3$, and $A_4$, on each monomer unit, independently, is C or N; each $G_1$, $G_2$, $G_3$, and $G_4$, on each monomer unit, independently, is selected from the group consisting of H, solubilizing side groups, reactive side groups, and reactive solubilizing side groups, provided that (1) at least one monomer unit has at least one solubilizing side group and at least one reactive side group, or (2) at least one monomer unit has at least one reactive solubilizing side group, and provided that when any of $A_1$, $A_2$, $A_3$, and $A_4$ is N, the corresponding $G_1$, $G_2$, $G_3$, or $G_4$ is nil; the macromonomer has a degree of polymerization, $DP_n$, greater than about 6; and adjacent monomer units are oriented head-to-head, head-to-tail, or randomly; and at least one monomer having at least one reactive group complementary to at least one reactive side group or reactive solubilizing side group on the macromonomer.

2. A polymer according to claim 1, wherein said at least one reactive side group on the macromonomer is selected from the group consisting of acetals, acetals from ethylvinylether, acetylenes, acetyls, acid anhydrides, acids, acrylamides, acrylates, alcohols, aldehydes, alkanols, alkyl aldehydes, alkyl halides, amides, amines, anilines, aryl aldehydes, azides, benzocyclobutenes, biphenylenes, carboxylates, carboxylic acids and their salts, carboxylic acid halides, carboxylic anhydrides, cyanates, cyanides, epoxides, esters, ethers, formyls, fulvenes, halides, heteroaryls, hydrazines, hydroxylamines, imides, imines, isocyanates, ketals, ketoalkyls, ketoaryls, ketones, maleimides, nadimides, nitriles, olefins, phenols, phosphates, phosphonates, quaternary amines, silanes, silicates, silicones, silyl ethers, styrenes, sulfonamides, sulfones, sulfonic acids and their salts, sulfonyl halides, sulfoxides, tetrahydropyranyl ethers, urethanes, vinyl ethers, thioethers, and vinyls.

3. A mixture composition comprising:
   a macromonomer having the structure

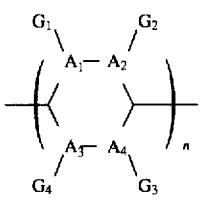

wherein each $A_1$, $A_2$, $A_3$, and $A_4$, on each monomer unit, independently, is C or N; each $G_1$, $G_2$, $G_3$, and $G_4$, on each monomer unit, independently, is selected from the group consisting of H, solubilizing side groups, reactive side groups, and reactive solubilizing side groups, provided that (1) at least one monomer unit has at least one solubilizing side group and at least one reactive side group, or (2) at least one monomer unit has at least one reactive solubilizing side group, and provided that when any of $A_1$, $A_2$, $A_3$, and $A_4$ is N, the corresponding $G_1$, $G_2$, $G_3$, or $G_4$ is nil; the macromonomer has a degree of polymerization, $DP_n$, greater than about 6; and adjacent monomer units are oriented head-to-head, head-to-tail, or randomly; and at least one complementary condensation monomer.

4. A polymer according to claim 3, wherein said at least one condensation monomer is selected from the group consisting of p-phenylenediamine, m-phenylenediamine, oxydianiline, methylenedianiline, terephthalic acid, terephthaloyl chloride, esters of terepthalic acids, and mixtures thereof.

5. A polymer according to claim 4, wherein said at least one condensation monomer is selected from the group consisting of hexamethylenediamine, adipic acid, esters of adipic acid, and adipoyl chloride.

6. A polymer according to claim 3, wherein said at least one complementary condensation monomer is selected from the group consisting of amino acids, biscarboxylic acids, biscarboxylic acid chlorides, biscarboxylic acid esters, diamines, diols, hydroxycarboxylic acids, lactams, and lactones.

7. A polymer according to claim 3, wherein said at least one complementary condensation monomer comprises terephthalic acid and ethylene glycol.

8. A reinforced polymeric composition comprising:

a macromonomer having the structure

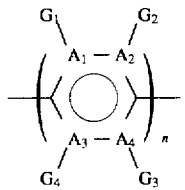

wherein each $A_1$, $A_2$, $A_3$, and $A_4$, on each monomer unit, independently, is C or N; each $G_1$, $G_2$, $G_3$, and $G_4$, on each monomer unit, independently, is selected from the group consisting of H, solubilizing side groups, reactive side groups, and reactive solubilizing side groups, provided that (1) at least one monomer unit has at least one solubilizing side group and at least one reactive side group, or (2) at least one monomer unit has at least one reactive solubilizing side group, and provided that when any of $A_1$, $A_2$, $A_3$, and $A_4$ is N, the corresponding $G_1$, $G_2$, $G_3$, or $G_4$ is nil; the macromonomer has a degree of polymerization, $DP_n$, greater than about 6; and adjacent monomer units are oriented head-to-head, head-to-tail, or randomly; and, in addition to any such reactive side groups and reactive solubilizing side groups, at least one flexible polymer covalently attached to the macromonomer.

9. A reinforced polymer according to claim 8, wherein the flexible polymer is selected from the group consisting of polyacetals, polyamides, polyimides, polyesters, polycarbonates, polyamide-imides, polyamide-esters, polyamide-ethers, polycarbonate-esters, polyamide-ethers, polyalkylmethacrylates, polyethylene, polypropylene, polystyrene, polyvinylacetate, polyvinylchloride, and polyvinylalcohol.

10. A polymeric composition according to claim 8, wherein the flexible polymer is a polyamide and the composition is formed by mixing the macromonomer with monomers capable of forming polyaimdes and a catalyst, followed by polymerization thereof.

11. A polymer composition according to claim 8, wherein the flexible polymer is a polyacrylate, and the composition is formed by mixing the macromonomers with acrylate monomers and initiators, followed by polymerization thereof.

12. A thermoset composition comprising:

a product obtained by curing a macromonomer having the structure

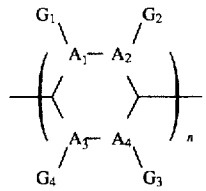

wherein each $A_1$, $A_2$, $A_3$, and $A_4$, on each monomer unit, independently, is C or N; each $G_1$, $G_2$, $G_3$, and $G_4$, on each monomer unit, independently, is selected from the group consisting of H, solubilizing side groups, reactive side groups, and reactive solubilizing side groups, provided that (1) at least one monomer unit has at least one solubilizing side group and at least one reactive side group, or (2) at least one monomer unit has at least one reactive solubilizing side group, and provided that when any of $A_1$, $A_2$, $A_3$, and $A_4$ is N, the corresponding $G_1$, $G_2$, $G_3$, or $G_4$ is nil; the macromonomer has a degree of polymerization, $DP_n$, greater than about 6; and adjacent monomer units are oriented head-to-head, head-to-tail, or randomly;

with a curing agent having reactive groups complementary to the reactive side groups, reactive solubilizing side groups, or both reactive side groups and reactive solubilizing side groups of the macromonomer and capable of forming covalent crosslinks therewith.

13. A thermoset composition according to claim 12, wherein said at least one reactive side group or reactive solubilizing side group is selected from the group consisting of acetylenes, acrylates, alcohols, amine derived groups, anilines, benzocyclobutenes, biphenylenes, epoxides, isocyanates, maleimides, nadimides, phenols and vinyls.

14. A thermoset composition according to claim 12, wherein the curing agent is selected from the group consisting of diamines, polyamines, diols, polyols, diepoxides, and polyepoxides.

15. A thermoset composition formed by thermally curing macromonomers having the structure

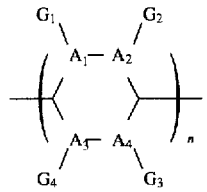

wherein each $A_1$, $A_2$, $A_3$, and $A_4$, on each monomer unit, independently, is C or N; each $G_1$, $G_2$, $G_3$, and $G_4$, on each monomer unit, independently, is selected from the group consisting of H, solubilizing side groups, reactive side groups, and reactive solubilizing side groups, provided that (1) at least one monomer unit has at least one solubilizing side group and at least one reactive side group, or (2) at least one monomer unit has at least one reactive solubilizing side group, and provided that when any of $A_1$, $A_2$, $A_3$, and $A_4$ is N, the corresponding $G_1$, $G_2$, $G_3$, or $G_4$ is nil; the macromonomer has a degree of polymerization, $DP_n$, greater than about 6; and adjacent monomer units are oriented head-to-head, head-to-tail, or randomly.

16. A thermoset according to claim 15, wherein said at least one reactive side group or reactive solubilizing side group is selected from the group consisting of acetylenes, benzocyclobutenes, biphenylenes, maleimides, and nadimides.

17. A mixture composition comprising:

a macromonomer having the structure

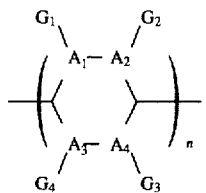

wherein each $A_1$, $A_2$, $A_3$, and $A_4$, on each monomer unit, independently, is C or N; each $G_1$, $G_2$, $G_3$, and $G_4$, on each monomer unit, independently, is selected from the group consisting of H, solubilizing side groups, reactive side groups, and reactive solubilizing side groups, provided that (1) at least one monomer unit has at least one solubilizing side group and at least one reactive side group, or (2) at least one monomer unit has at least one reactive solubilizing side group, and provided that when any of $A_1$, $A_2$, $A_3$, and $A_4$ is N, the corresponding $G_1$, $G_2$, $G_3$, or $G_4$ is nil; the macromonomer has a degree of polymerization, $DP_n$, greater than about 6; and adjacent monomer units are oriented head-to-head, head-to-tail, or randomly; and at least one addition monomer.

18. A reinforced polymeric material according to claim 17, wherein said at least one addition monomer is selected from the group consisting of alkylmethacrylates, butadiene, dicyclopentadiene, ethylene, propylene, styrene, tetrafluoroethylene, vinyl acetate and vinyl chloride.

19. A reinforced polymer elastomer comprising:

an elastomer having a polymer network; and rigid segments covalently attached to the polymer network, derived from macromonomers having the structure

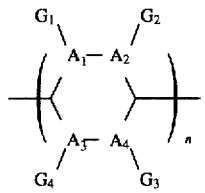

wherein each $A_1$, $A_2$, $A_3$, and $A_4$, on each monomer unit, independently, is C or N; each $G_1$, $G_2$, $G_3$, and $G_4$, on each monomer unit, independently, is selected from the group consisting of H, solubilizing side groups, reactive side groups, and reactive solubilizing side groups, provided that (1) at least one monomer unit has at least one solubilizing side group and at least one reactive side group, or (2) at least one monomer unit has at least one reactive solubilizing side group, and provided that when any of $A_1$, $A_2$, $A_3$, and $A_4$ is N, the corresponding $G_1$, $G_2$, $G_3$, or $G_4$ is nil; the macromonomer has a degree of polymerization, $DP_n$, greater than about 6; and adjacent monomer units are oriented head-to-head, head-to-tail, or randomly.

20. A reinforced polymer elastomer according to claim 19, wherein the elastomer is selected from the group consisting of polybutadiene, copolymers of butadiene with one or more other monomers, butadiene-acrylonitrile rubber, styrene-butadiene rubber, polyisoprene, copolymers of isoprene with one or more other monomers, polyphosphazenes, natural rubber, and blends of natural and synthetic rubber.

21. A reinforced polymer elastomer according to claim 19, wherein the elastomer is selected from the group consisting of polydimethylsiloxane, copolymers containing the dimethylsiloxane unit, polydiphenylsiloxane, and copolymers containing the diphenylsiloxane unit.

* * * * *

UNITED STATES PATENT AND TRADEMARK OFFICE
CERTIFICATE OF CORRECTION

PATENT NO. : 5,539,048
DATED : July 23, 1996
INVENTOR(S) : Robert R. Gagné; Matthew L. Marrocco, III; Mark S. Trimmer; Neil H. Hendricks It is certified that error appears in the above-indentified patent and that said Letters Patent is hereby corrected as shown below:

On the title page, Item [56], U.S. Patent Documents, change
"3,792,099 7/1974 Wang et al. .... 529/396" to
--3,792,099 7/1972 Wang et al. .... 529/396.

Column 2, line 50, after "invention)," insert -- now U.S. Patent No. 5,227,457, --
Column 4, line 46, change "Units" to -- units --
Column 4, lines 57-64, the structure should appear as follows:

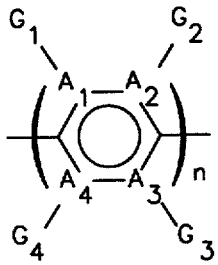

Column 11, line 57, after "macromonomers of" insert -- the --
Column 13, line 36, after "fire resistance" insert -- , --.
Column 13, line 40, change "rigid red" to -- rigid rod --.

UNITED STATES PATENT AND TRADEMARK OFFICE
CERTIFICATE OF CORRECTION

PATENT NO. : 5,539,048
DATED : July 23, 1996
INVENTOR(S) : Robert R. Gagné; Matthew L. Marrocco, III; Mark S. Trimmer; Neil H. Hendricks It is certified that error appears in the above-indentified patent and that said Letters Patent is hereby corrected as shown below:

Column 23, line 37, change "abut" to -- about --.
Column 25, line 23, change "HCL" to -- HCl --
Column 30, claim 1, lines 10-17, the structure should appear as follows:

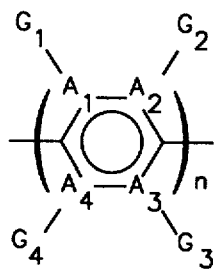

Column 30, claim 3, lines 55-61, the structure should appear as follows:

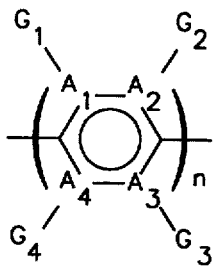

UNITED STATES PATENT AND TRADEMARK OFFICE
CERTIFICATE OF CORRECTION

PATENT NO. : 5,539,048
DATED : July 23, 1996
INVENTOR(S) : Robert R. Gagné; Matthew L. Marrocco, III;
Mark S. Trimmer; Neil H. Hendricks It is certified that error appears in the above-indentified patent and that said Letters Patent is hereby corrected as shown below:

Column 31, claim 8, lines 30-37, the structure should appear as follows:

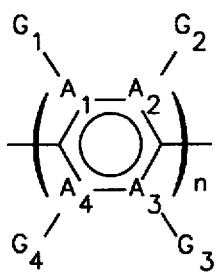

Column 31, line 66, change "polyaimdes" to -- polyamides --.

Column 32, claim 12, lines 9-16, the structure should appear as follows:

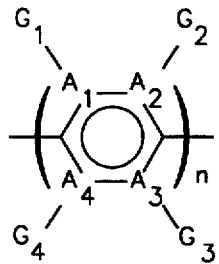

UNITED STATES PATENT AND TRADEMARK OFFICE
CERTIFICATE OF CORRECTION

PATENT NO. : 5,539,048
DATED : July 23, 1996
INVENTOR(S) : Robert R. Gagné; Matthew L. Marrocco, III; Mark S. Trimmer; Neil H. Hendricks It is certified that error appears in the above-indentified patent and that said Letters Patent is hereby corrected as shown below:

Column 32, claim 15, lines 48-55, the structure should appear as follows:

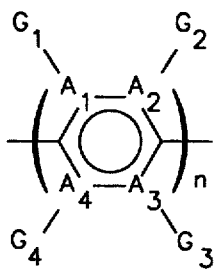

Column 33, claim 17, lines 10-17, the structure should appear as follows:

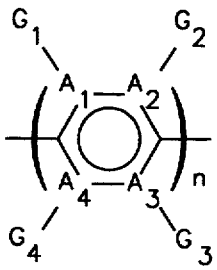

UNITED STATES PATENT AND TRADEMARK OFFICE
CERTIFICATE OF CORRECTION

PATENT NO. : 5,539,048
DATED : July 23, 1996
INVENTOR(S) : Robert R. Gagné; Matthew L. Marrocco, III;
Mark S. Trimmer; Neil H. Hendricks It is certified that error appears in the above-indentified patent and that said Letters Patent is hereby corrected as shown below:

Column 34, claim 19, lines 4-11, the structure should appear as follows:

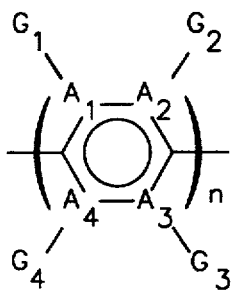

Signed and Sealed this

Seventh Day of October, 1997

*Attest:*

BRUCE LEHMAN

*Attesting Officer*  Commissioner of Patents and Trademarks

UNITED STATES PATENT AND TRADEMARK OFFICE
CERTIFICATE OF CORRECTION

PATENT NO. : 5,539,048
DATED : July 23, 1996
INVENTOR(S) : Robert R. Gagné; Matthew L. Marrocco, III;
Mark S. Trimmer; Neil H. Hendricks It is certified that error appears in the above-identified patent and that said Letters Patent is hereby corrected as shown below:

Column 31, line 10, claim 4, delete "polymer" and insert therefor
-- mixture composition --.
Column 31, line 15, claim 5, delete "polymer" and insert therefor
-- mixture composition --.
Column 31, line 19, claim 6, delete "polymer" and insert therefor
-- mixture composition --.
Column 31, line 25, claim 7, delete "polymer" and insert therefor
-- mixture composition --.
Column 31, line 56, claim 9, delete "polymer" and insert therefor
-- polymeric composition --.
Column 31, line 63, claim 10, after "A" and before "polymeric" insert
-- reinforced --.
Column 32, line 1, claim 11, delete "polymer" and insert therefor
-- reinforced polymeric --.
Column 33, line 32, claim 18, delete "reinforced polymeric material" and
insert therefor -- mixture composition --.

Signed and Sealed this

Seventh Day of July, 1998

Attest:

BRUCE LEHMAN

*Attesting Officer*   *Commissioner of Patents and Trademarks*